(12) United States Patent
Ward et al.

(10) Patent No.: US 12,137,925 B2
(45) Date of Patent: *Nov. 12, 2024

(54) FORCEPS INCLUDING A PRE-LOADED HANDLE LATCH

(71) Applicant: GYRUS ACMI, INC., Westborough, MA (US)

(72) Inventors: Zane R. Ward, Minneapolis, MN (US); John Mensch, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 18/314,351

(22) Filed: May 9, 2023

(65) Prior Publication Data
US 2023/0389949 A1    Dec. 7, 2023

Related U.S. Application Data

(63) Continuation of application No. 17/081,760, filed on Oct. 27, 2020, now Pat. No. 11,678,900, which is a
(Continued)

(51) Int. Cl.
*A61B 17/28* (2006.01)
*A61B 18/14* (2006.01)
(Continued)

(52) U.S. Cl.
CPC ...... *A61B 17/2833* (2013.01); *A61B 18/1445* (2013.01); *A61B 90/08* (2016.02);
(Continued)

(58) Field of Classification Search
CPC ............ A61B 17/2909; A61B 18/1445; A61B 2017/2946; A61B 2018/1455;
(Continued)

(56) References Cited

U.S. PATENT DOCUMENTS

| | | | |
|---|---|---|---|
| 1,198,958 A | 9/1916 | Risley |
| 2,042,985 A | 6/1936 | Gardella |

(Continued)

FOREIGN PATENT DOCUMENTS

| | | | |
|---|---|---|---|
| CN | 105188573 A | 12/2015 |
| CN | 110403668 A | 11/2019 |

(Continued)

OTHER PUBLICATIONS

U.S. Appl. No. 15/967,491 U.S. Pat. No. 10,842,516, filed Apr. 30, 2018, Forceps Including a Pre-Loaded Handle Latch.
(Continued)

*Primary Examiner* — Katherine M Shi
(74) *Attorney, Agent, or Firm* — Schwegman Lundberg & Woessner, P.A.

(57) ABSTRACT

A surgical device comprising: a closure assembly comprising: (a) a movement unit including (i) a bar and (ii) a contact element, wherein the bar, the contact element, or both move in a direction of a prescribed motion; (b) a latch unit comprising: (i) a latch plate including: (1) a hook latch that selectively receives the bar, the latch plate being movable between: (A) a lockable state where the hook latch is engageable by the bar, and (B) an unlockable state where the hook latch is unengageable by the bar; (c) an indicator mechanism that moves into alignment with the prescribed motion of the contact element, the bar, or both when the latch unit is in the unlockable state so that the indicator is contacted by the bar, the contacting element, or both generating an indication.

20 Claims, 12 Drawing Sheets

Related U.S. Application Data continuation of application No. 15/967,491, filed on Apr. 30, 2018, now Pat. No. 10,842,516.

(51) Int. Cl.
*A61B 90/00* (2016.01)
*A61B 17/00* (2006.01)

(52) U.S. Cl.
CPC ............... *A61B 2017/00115* (2013.01); *A61B 2018/1452* (2013.01); *A61B 2090/0811* (2016.02)

(58) Field of Classification Search
CPC ............ A61B 18/1447; A61B 17/2833; A61B 2018/00601; A61B 2018/1412; A61B 2018/1452; A61B 10/06; A61B 17/29; A61B 17/295; A61B 17/32; A61B 17/320016; A61B 17/3201; A61B 18/1442; A61B 2017/00115; A61B 2017/00424; A61B 2017/0046; A61B 2017/2837; A61B 2017/2925
See application file for complete search history.

(56) References Cited

U.S. PATENT DOCUMENTS

| | | |
|---|---|---|
| 2,214,984 A | 9/1940 | Henry |
| 2,381,084 A | 8/1945 | Slad |
| 2,894,424 A | 7/1959 | Vaughan, Jr. |
| 3,189,374 A | 6/1965 | Mertes |
| 3,399,583 A | 9/1968 | Lance |
| 3,465,621 A | 9/1969 | Ladd |
| 3,643,663 A | 2/1972 | Sutter |
| 3,694,015 A | 9/1972 | Gley |
| 3,699,632 A | 10/1972 | Anhalt |
| 3,819,282 A | 6/1974 | Schultz |
| 3,913,586 A | 10/1975 | Baumgarten |
| 4,215,884 A | 8/1980 | Little |
| 4,318,313 A | 3/1982 | Tartaglia |
| 4,449,022 A | 5/1984 | Uno et al. |
| 4,494,543 A | 1/1985 | Hart |
| 4,792,165 A | 12/1988 | Nishimura |
| 5,104,397 A | 4/1992 | Vasconcelos et al. |
| 5,176,702 A | 1/1993 | Bales et al. |
| 5,211,655 A | 5/1993 | Hasson |
| 5,358,292 A | 10/1994 | Van Wiebe et al. |
| 5,425,743 A | 6/1995 | Nicholas |
| 5,498,039 A | 3/1996 | Bivens |
| 5,499,998 A | 3/1996 | Meade |
| 5,735,849 A | 4/1998 | Baden et al. |
| 5,884,954 A | 3/1999 | Trozera |
| 6,050,996 A | 4/2000 | Schmaltz et al. |
| 6,056,333 A | 5/2000 | Wach |
| 6,247,733 B1 | 6/2001 | Weiland |
| 6,585,735 B1 | 7/2003 | Frazier et al. |
| 6,669,250 B1 | 12/2003 | St. Louis |
| 6,799,705 B1 | 10/2004 | Lutoslawski |
| 7,115,139 B2 | 10/2006 | Mcclurken et al. |
| 7,118,587 B2 | 10/2006 | Dycus et al. |
| 7,150,749 B2 | 12/2006 | Dycus et al. |
| 7,201,411 B2 | 4/2007 | Bella et al. |
| 7,232,440 B2 | 6/2007 | Dumbauld et al. |
| 7,766,910 B2 | 8/2010 | Hixson et al. |
| 7,793,995 B2 | 9/2010 | King et al. |
| 7,802,856 B2 | 9/2010 | Hashemi et al. |
| 8,109,582 B2 | 2/2012 | Dubach |
| 8,246,094 B2 | 8/2012 | Long et al. |
| 8,251,994 B2 | 8/2012 | Mckenna et al. |
| 8,328,170 B2 | 12/2012 | Wasinger |
| 8,398,620 B2 | 3/2013 | Bacher et al. |
| 8,945,175 B2 | 2/2015 | Twomey |
| 9,452,011 B2 | 9/2016 | Batchelor et al. |
| 9,851,741 B2 | 12/2017 | Lamser et al. |
| 10,842,516 B2 | 11/2020 | Ward et al. |
| 11,678,900 B2 | 6/2023 | Ward et al. |
| 2002/0016609 A1 | 2/2002 | Wensel et al. |
| 2005/0277954 A1 | 12/2005 | Smith et al. |
| 2006/0190035 A1 | 8/2006 | Hushka et al. |
| 2006/0208506 A1 | 9/2006 | Kern et al. |
| 2008/0154300 A1 | 6/2008 | Jabbour |
| 2011/0301637 A1 | 12/2011 | Kerr et al. |
| 2012/0109187 A1 | 5/2012 | Gerhardt, Jr. et al. |
| 2012/0184989 A1 | 7/2012 | Twomey |
| 2012/0184990 A1 | 7/2012 | Twomey |
| 2012/0191091 A1 | 7/2012 | Allen |
| 2013/0066317 A1 | 3/2013 | Evans et al. |
| 2013/0178852 A1 | 7/2013 | Allen, IV et al. |
| 2013/0325057 A1 | 12/2013 | Larson et al. |
| 2014/0135805 A1 | 5/2014 | Windgassen et al. |
| 2014/0236156 A1 | 8/2014 | Arlettaz et al. |
| 2014/0276795 A1 | 9/2014 | Batchelor et al. |
| 2015/0331443 A1 | 11/2015 | Lamser et al. |
| 2016/0051275 A1 | 2/2016 | Batchelor et al. |
| 2016/0338763 A1 | 11/2016 | Allen, IV et al. |
| 2019/0328413 A1 | 10/2019 | Ward et al. |
| 2021/0077136 A1 | 3/2021 | Ward et al. |

FOREIGN PATENT DOCUMENTS

| | | |
|---|---|---|
| CN | 110403668 B | 7/2022 |
| CN | 115462870 A | 12/2022 |
| EP | 0392548 A1 | 10/1990 |
| EP | 0908152 A1 | 4/1999 |
| EP | 2364651 A1 | 9/2011 |
| EP | 3563780 A1 | 11/2019 |
| EP | 3563780 B1 | 12/2020 |
| EP | 3824825 B1 | 12/2023 |
| GB | 2546268 A | 7/2017 |

OTHER PUBLICATIONS

U.S. Appl. No. 17/081,760 U.S. Pat. No. 11,678,900, filed Oct. 27, 2020, Forceps Including a Pre-Loaded Handle Latch.
"European Application Serial No. 23214751.2, Invitation to remedy deficiencies (R. 58 EPC) mailed Jan. 17, 2024", 1 page.
"European Application Serial No. 23217773.3, Response filed Mar. 15, 2024 to Invitation to remedy deficiencies (R. 58 EPC) mailed Jan. 17, 2024", 5 pgs.
"U.S. Appl. No. 15/967,491, Non Final Office Action mailed Mar. 23, 2020", 6 pgs.
"U.S. Appl. No. 15/967,491, Notice of Allowance mailed Jul. 21, 2020", 8 pgs.
"U.S. Appl. No. 15/967,491, Response filed Jun. 23, 2020 to Non Final Office Action mailed Mar. 23, 2020", 9 pgs.
"U.S. Appl. No. 17/081,760, Notice of Allowance mailed Feb. 13, 2023", 13 pgs.
"U.S. Appl. No. 17/081,760, Preliminary Amendment filed Dec. 11, 2020", 7 pgs.
"Chinese Application Serial No. 201910171384.6, Office Action mailed Jan. 5, 2022", W/English Translation, 10 pgs.
"Chinese Application Serial No. 201910171384.6, Response filed Feb. 24, 2022 to Office Action mailed Jan. 5, 2022", w/English claims, 41 pgs.
"Closure Assembly That is Laterally Movable for Selective Locking", Potentially related U.S. Appl. No. 15/941,128, filed Mar. 30, 2018, 39 pgs.
"Endoscopic Cutting Forceps With Jaw Clamp Lever Latching Mechanism", Potentially related U.S. Appl. No. 14/706,146, filed May 7, 2015, 40 pgs.
"European Application Serial No. 19168273.1, Extended European Search Report mailed Jul. 31, 2019", 7 pgs.
"European Application Serial No. 19168273.1, Response filed Apr. 17, 2020 to Extended European Search Report mailed Jul. 31, 2019", 78 pgs.
"European Application Serial No. 20212072.1, Communication Pursuant to Article 94(3) EPC mailed Jan. 7, 2022", 4 pgs.
"European Application Serial No. 20212072.1, Extended European Search Report mailed Apr. 7, 2021", 6 pgs.

(56) References Cited

OTHER PUBLICATIONS

"European Application Serial No. 20212072.1, Invitation pursuant to Article 94(3) and Rule 71(1) EPC mailed Jan. 11, 2023", 4 pgs.

"European Application Serial No. 20212072.1, Response filed May 3, 2022 to Communication Pursuant to Article 94(3) EPC mailed Jan. 7, 2022", 71 pgs.

"European Application Serial No. 20212072.1, Response filed May 16, 2023 to Invitation pursuant to Article 94(3) and Rule 71(1) EPC mailed Jan. 11, 2023", 6 pgs.

"European Application Serial No. 20212072.1, Response filed Nov. 24, 2021 to Extended European Search Report mailed Apr. 7, 2021", w/ English Claims, 8 pgs.

"Forceps Including a Double Biased Handle Latch", Potentially related U.S. Appl. No. 15/941,590, filed Mar. 30, 2018, 48 pgs.

"Forceps Including a Pre-Loaded Handle Latch", Potentially related U.S. Appl. No. 15/941,205, filed Mar. 30, 2018, 42 pgs.

"HALO Cutting Forceps", Olympus, [Online] Retrieved from the internet: <http://www.olympusamerica.com/msg_section/envision/oneoffpages/files/Halo_PKS_Brochure.pdf> (Last Accessed May 14, 2018), (Apr. 3, 2014), 2 pgs.

"European Application Serial No. 23214751.2, Extended European Search Report mailed Jun. 26, 2024", 7 pgs.

FORCEPS INCLUDING A PRE-LOADED HANDLE LATCH

CROSS-REFERENCE TO RELATED APPLICATIONS

This application is a Continuation of U.S. patent application Ser. No. 17/081,760, filed Oct. 27, 2020 and now issued as U.S. Pat. No. 11,678,900, which is a Continuation of U.S. patent application Ser. No. 15/967,491, filed Apr. 30, 2018 and now issued as U.S. Pat. No. 10,842,516; the contents of which are incorporated herein by reference in their entireties.

FIELD

The present teachings relate to forceps with a first jaw and a second jaw that are movable relative to each other and the forceps include a closure assembly having a movement unit and a latch unit that when connected prevent movement of the first jaw to the second jaw, and specifically an indicator that indicates a locked position of the jaws when the latch unit is in the unlockable state.

BACKGROUND

Generally, forceps may be utilized for laparoscopic surgery or open surgery. The forceps may be used to control delicate movements inside a patient. These forceps may be used to grip an anatomical feature. The forceps may include a gripping assembly or a cutting assembly. The forceps may include electrical energy for use in the gripping assembly, the cutting assembly, or both. The forceps have a pair of opposed resilient jaws that are closed against each other or a cutting blade. The jaws of the forceps may be locked together so that the surgeon may lock the forceps on a feature of interest while the surgeon works on a different anatomical feature or uses a different instrument. The forceps may include an unlocked state where the first working arm and the second working arm may be freely moved relative to each other. Examples of some latches or forceps including locks may be found in U.S. Pat. Nos. 5,104,397; 6,056,333; 6,247,733; 7,802,856; and 8,945,175 and U.S. Patent Application Publication No.: 201310066317; 2014/0276795; 2015/0331443; 2016/0051275 all of which are incorporated by reference herein in their entirety for all purposes. During an unlocked state the surgeon may not be able to see the position of the jaws relative to each other and thus, the surgeon may not be able to ascertain when the jaws are fully closed, clamped, closed, at a locked position, or a combination thereof based upon a position of a handle.

It would be attractive for the forceps to include one or more closure assemblies that lock one or more working arms together when the closure assemblies are in a lockable state and one or more indicator mechanisms that indicate one or more positions of the working arms, the closure assembly, or both. What is needed is an indicator mechanism that indicates a locked state position of the working arms when the closure assembly is in the unlatchable state. What is needed is an indicator mechanism that provides an audible indication, a tactile indication, or both when the indicator mechanism reaches a predetermined location. It would be attractive to have an indicator mechanism that indicated one or more positions of a closure assembly.

SUMMARY

The disclosure meets one or more of the needs by providing: a closure assembly comprising a latch unit, a movement unit, and an indicator mechanism that indicates one or more positions of the latch unit relative to the movement unit. The movement unit is connected to a movable member that moves along a prescribed path. The latch unit is connected to a ground member and the latch unit is movable relative to the ground member. The latch unit includes a bias member that is pre-loaded when the bias member is located within the latch unit and the latch unit is located in a home position. The latch unit includes the indicator mechanism and the indicator mechanism indicates a position of the movement unit or a bar of the movement unit as the bar is moved along a prescribed path. The bias member increases in a load relative to the pre-load when the latch unit is moved in the first direction away from the home position and the second direction away from the home position and the indicator mechanism indicates a position of the bar as the bias member is moved in the first direction, the second direction, is not moved, or a combination thereof.

The present teachings provide a surgical device comprising: a closure assembly comprising: (a) a movement unit including (i) a bar and (ii) a contact element, wherein the bar, the contact element, or both move in a direction of a prescribed motion; (b) a latch unit comprising: (i) a latch plate including: (1) a hook latch that selectively receives the bar, the latch plate being movable between: (A) a lockable state where the hook latch is engageable by the bar, and (B) an unlockable state where the hook latch is unengageable by the bar; (c) an indicator mechanism that moves into alignment with the prescribed motion of the contact element, the bar, or both when the latch unit is in the unlockable state so that the indicator is contacted by the bar, the contacting element, or both generating an indication.

The present teachings provide the forceps to include one or more closure assemblies that lock one or more working arms together when the closure assemblies are in a lockable state and one or more indicator mechanisms that indicate one or more positions of the working arms, the closure assembly, or both. The present teachings provide an indicator mechanism that indicates a locked state position of the working arms when the closure assembly is in the unlatchable state. The present teachings provide an indicator mechanism that provides an audible indication, a tactile indication, or both when the indicator mechanism reaches a predetermined location. The present teachings provide an indicator mechanism that indicated one or more positions of a closure assembly.

DETAILED DESCRIPTION

Figure 1:
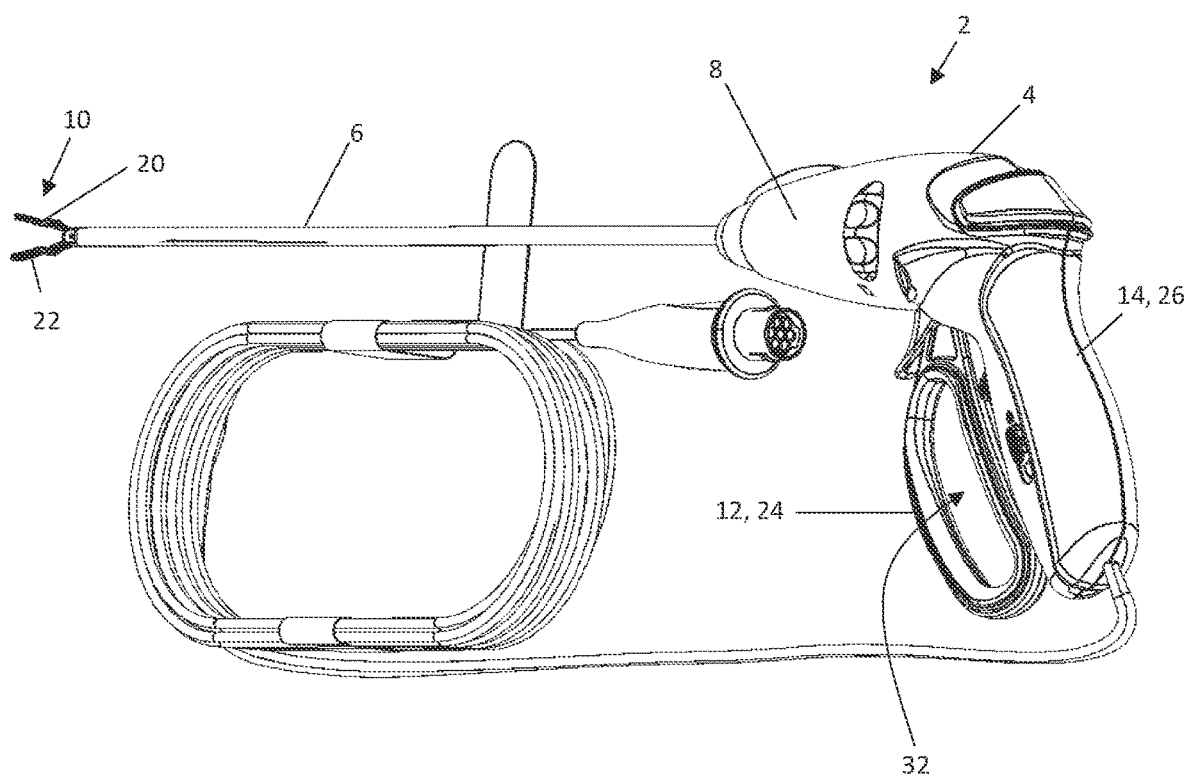
FIG. 1 illustrates a rear perspective view of an electrosurgical device.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a closure assembly that connects two or more members together and prevents movement of the two members relative to each other. The closure assembly may connect a movable member to a ground member or connect two movable members together. The closure assembly may prevent movement of a door (e.g., movable member) relative to storage space (e.g., ground member). The closure assembly may be deactivated (e.g., switched to an unlockable state). The closure assembly may be part of a hand-held device, pliers, clamps, or a combination thereof. The closure assembly may be part of a drawer, cabinet, bin, a door, or a combination thereof. Preferably, the closure assembly is part of a surgical device and prevents arms that control forceps from moving relative to each other.

The present teachings relate to a surgical device. The surgical device may be a non-electrical device (i.e., may only provide mechanical functions such as mechanical cutting or gripping). Preferably, the surgical device is an electrosurgical device. The electrosurgical device may provide one or more therapy currents. Preferably, the electrosurgical device provides two or more therapy currents (e.g., monopolar power and bipolar power). A therapy current may pass between the jaws (e.g., bipolar power). A therapy current may pass from a jaw to a blade or vice versa. A therapy current (e.g., monopolar power) may pass from a blade to a remote electrode (e.g., ground pad). The electrosurgical device may apply power before, after, or simultaneously with a mechanical technique (e.g., gripping or cutting). When power is applied an anatomical feature may be cut, cauterized, sealed, coagulated, or a combination thereof. The electrosurgical device may include a distal end and a proximal end. The distal end may include a portion of a forceps device (e.g., jaws, blade, or both). The distal end may be a portion of the surgical device that is farthest from a user. The proximal end may be a portion a user grips (e.g., hand piece or housing) or a portion closest to a user.

The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may assist in applying a therapy current to a feature of interest. The forceps may move between a first position (e.g., release position) and a second position (e.g., gripping position). The forceps may function to be used in surgery, for example laparoscopic surgery. The forceps may be used with or without power. The forceps may include a first working arm with a jaw and a second working arm with a jaw. The forceps may be comprised of parts needed to perform the recited functions and may include generally, a stylet (e.g., a tubular member, a hollow tube, or an assembly of tubes), a hand piece, one or more operable mechanisms used to actuate the stylet, two or more jaws, two or more working arms, or a combination thereof.

The two or more working arms may function to move towards and away from each other to assist a user in gripping a feature of interest. The two or more working arms may be directly biased towards each other by a user. Preferably, the two or more working arms are biased towards each other by a stylet or tube moving over the arms (e.g., distally) so that the arms are moved together. The two or more working arms may be moved towards each other by being retracted into a stylet or tube. The working arms may be solid and rotate about a pivot. The working arms may be a wire that is shaped to create a working arm, a jaw, or both. Each of the two or more working arms may include a jaw.

The two or more opposing jaws may function to create a gripping force, grip a feature of interest, or both. The two or more opposing jaws may move towards each other (e.g. laterally) to create a gripping force, to grip a feature of interest, or both. The two or more opposing jaws may function to be used to grip or clamp an item of interest for cutting or applying a bipolar energy source. Preferably, the two or more opposing jaws may be one jaw structure with another mirror image opposing jaw structure (i.e., identical) that when forced together may create a gripping function. The two opposing jaws may be formed of two wires that are shaped to have a generally "U" shaped end. The two opposing jaws may be made of a flexible material, resilient material, rigid stainless steel, a plastically deformable material, an elastically deformable material, or a combination thereof. The two opposing jaws may be made of a material that conducts electricity. The two opposing jaws may include a channel (e.g., a blade track) to allow for a cutting instrument to be inserted while retaining functionality of the two or more opposing jaws.

The two opposing jaws may be used to apply electricity to a feature of interest that may be gripped by the two opposing jaws. The two opposing jaws may be a first jaw and a second jaw. A closure assembly may lock the two opposing jaws together, lock the two opposing jaws on tissue, lock the two opposing jaws on a blade, or a combination thereof.

The blade may function to cut a feature of interest. The blade may be made of any material that may be sharpened; is strong enough to cut a feature of interest; is biocompatible; that may conduct electricity; or a combination thereof.

The blade may mechanically cut, electrically cut, or both. The blade may be extended into, and retracted from, the channel in the two opposing jaws. The distal end of the blade may have a shaped edge (e.g., sharpened). The blade may extend flush with or distal of the jaws. The blade may conduct power. The blade may conduct a therapy current. The blade may conduct bipolar energy, monopolar energy, or both. All or a portion of the blade may extend out of the stylet between and past the jaws to cut a feature of interest.

The stylet as discussed herein may include one or more tubular members or may be a tubular member (i.e., tube). The stylet may include one or more tubes, one or more shafts, or both that may extend through the tubes. The stylet may include a tubular member and an inner tube. The stylet may include a tube that extends around all or a portion of an inner tube. The stylet may be a hollow tube with one or more shafts extending through the hollow tube. The stylet and its components may be made of any biocompatible material, for example, stainless steel, plastic, a synthetic material, a natural material, or a combination thereof. The one or more outer tubes and/or stylet may function to close the jaws, bias the jaws, or both. The one or more outer tubes and/or stylet may function to house one or more jaws, one or more blades, or both. The one or more inner tubes may be part of a tubular member or a stylet. The one or more forceps may be free of any tubes or tubular members. The one outer tubes of the stylet may assist in connecting the jaws, the blade, or both to the hand piece.

The hand piece may be an assembly of parts or housing structures capable of forming a structure with a cavity that a user holds in their hand. The hand piece may function to be gripped by a user. When gripped by a user a top or upper portion of the handpiece may be located up relative to a user's hand and the bottom or lower portion may be located down relative to a user's hand. The hand piece may function to hold or encapsulate one or more or a plurality of components of the surgical device such as the latch unit, the indicator mechanism, or both. The forceps may extend from the hand piece and may be actuated by one or more operable mechanisms located within the hand piece. The forceps may be actuated by movement of a trigger that is connected to the hand piece. The hand piece and the trigger may be biased apart. A bias device may extend between the hand piece and the trigger so that a gap is located between the hand piece and the trigger. A bias device may be located along the stylet, within the hand piece, in communication with a part that axially moves so that the working arms are moved together, or a combination thereof. The bias device may be a bias device taught herein including those taught in U.S. Pat. No. 9,851,741 regarding a compression spring or element 90 or the teachings of U.S. Pat. No. 5,735,849 regarding a torsion spring or element 80 the teachings of which are incorporated by reference herein for all purposes include those regarding how a moveable member is moved relative to a ground member and especially how a trigger is moved relative to a handle. The hand piece may include the latch unit and the trigger may include the movement unit and when the movement unit and the latch unit are not connected together the bias member may move the trigger to form the gap therebetween. The hand piece may be comprised of one or more housing structures. Preferably, the hand piece is two or more housing structures. The housing structures may be two plastic pieces that connect together to enclose an open space that receives components of the surgical device. The hand piece may be a ground member. The hand piece may be static. The hand piece may be a ground member that is static when a user applies a pressure to so that a movable member is moved relative to the ground member. The housing structures may form a cavity to house working assemblies of the forceps. The housing structures may be one or more housing structures and preferably two or more housing structures. The housing structures may be any device that includes a recess for receiving one or more components of the forceps. The housing structures may be a housing that houses all or a portion of one or more operable mechanisms, one or more valves, one or more fluid distribution systems, or a combination thereof.

The one or more housings may function to form a hand piece, enclose a portion of an operable mechanism, enclose a portion of a stylet, enclose one or more tubes, or a combination thereof. The one or more housings may be a left half and a right half. The housing may be multiple pieces that are connected together. The housing may be made of plastic. The housing may be a combination of plastic and metal. The housing may provide a stationary part (e.g., ground member) that a user grips while a user moves a trigger (e.g., movable member) to actuate the forceps, a blade, or both. Preferably, the housing is connected to two or more triggers that movably connect to the housing so that upon actuation the jaws, blade, fluid distribution system, or a combination thereof are moved or actuated by one of the two or more triggers. More preferably, the triggers are movable relative to the housing to actuate the jaws, blade, fluid distribution system, or a combination thereof. The housing may be connected to a first jaw, a second jaw, or both jaws of forceps and a direct force may be applied to the housings in order to move the forceps towards or apart from each other. The jaws, blade, fluid distribution system, or a combination thereof may be moved between a first position (release position) and a second position (retract position) by one or more operable mechanism or direct contact by a user. The housing may have a portion that is a handle that a user grips.

The handle may function to assist in actuation of the forceps, the blade, applying electricity, or a combination thereof. The handle may include a lock, a lock plate, all or a portion of a closure assembly, a latch unit, or a combination thereof. The handle may be a proximal end of the surgical device. The handle may be a static member that one or more triggers move relative to. The handle may be a ground member that a movable member, a trigger, or both are movable relative to.

The ground member may function to be a movable member or a static member that another part (e.g., the movable member) is moved relative to. The ground member may be a central component fora coordinate system or a reference point for relative motion of other components of the device taught herein. The ground member may be connected to or located next to a movable member and function to prevent movement of another component such as forceps or a blade as the movable member moves relative to the ground member. The ground member may be part of a first working arm. The ground member may be a handle, a housing, a hand piece, a trigger, a jaw, or a combination thereof. The ground member may include all or a portion of a closure assembly. The ground member may include all of the latch unit, all of an indicator mechanism, or both. The ground member may receive a portion of a force to assist a movable member in being moved relative to the ground member. The ground member may receive a portion of the movable member to form a locked state.

The movable member may function to move relative to a ground member so that the forceps may be actuated, locked, released, or a combination thereof. The movable member may be biased apart from the ground member (e.g., a bias device may be located between the movable member and the ground member). The movable member may move with or relative to a ground member to lock, unlock, bias, or a combination thereof two or more jaws or two or more working arms. The movable member may move to open and close the jaws, move the blade, or both. The movable member may be a trigger. The movable member may be moved by a force of 1 N or more, about 2 N or more, about 3 N or more, or about 10 N or less. The movable member may be moved in the forward stroke, return stroke, or both with sufficient force to move the hook latch, move the indicator leg, or both. The movable member may include all or a portion of the closure assembly. The movable member may include the movement unit. The movable member may rotate about a pivot so that the movement unit moves along a movement path (e.g., prescribed motion). The movable member may be part of the closure assembly that assists in locking the jaws, the working arms, the surgical device, or a combination thereof.

The closure assembly may function to connect a movable member and a ground member together. The closure assembly may function to lock a first working arm to a second working arm, a first jaw to a second jaw, or both. The closure assembly may be movable between a lockable state and an unlockable state. The closure assembly may lock two items together when the closure assembly is in a locked state. The closure assembly may freely move as the movable member, the ground member, or both move relative to each other or are in an unlockable state. A portion of the closure assembly may be located on or within the movable member, the ground member, the movement unit, the latch unit, or a combination thereof. Preferably, the closure assembly includes a movement unit and a latch unit and one or more indicator mechanisms. More preferably, the closure assembly may be part of a ground member and a movable member and the movable member may be a trigger.

The one or more triggers function to be an input to an operable mechanism that moves one or both jaws, one or both working arms, or both. The one or more triggers may be a movable member or a ground member. Preferably, the triggers are a movable member and the ground is a handle or hand piece. The one or more triggers may be a cut trigger, a clamp trigger, an activation switch, or a combination thereof that when actuated inputs movement into an operable mechanism so that the operable mechanism provides an output. If the triggers are a lever, the lever is a rigid member that turns on a pivot. The cut lever, the clamp lever, or both may function to move one or more jaws, one or more blades, a jaw support rod, a blade support rod, a second link, one or more valves, or a combination thereof. The cut lever, the clamp lever, or both may extend between a release position (e.g., a start position) and a retract position (e.g., a full pull position where the jaws are closed, the blade is extended, or both). The cut lever and the clamp lever may be individually biased apart from the handle, the hand piece, or both. Preferably, the one or more triggers carry the movement unit so that the movement unit when in communication with the latch unit may restrict movement of the trigger.

The movement unit may be integrally connected to a movable member, a trigger, or both. The movement unit may extend from the movable member towards the ground member and even into the ground member. The movement unit may move in a prescribed motion. The prescribed motion may be a forward stroke and a return stroke. The forward stroke may be the movement member extending towards the ground member and the return stroke may be the movement member extending away from the ground member. The prescribed movement may be a linear motion, an arcuate movement, or a combination of both. The prescribed motion may overlap in a first direction and a second direction. The movement unit may rotate about a pivot so that the movement unit travels back and forth along a constant path (e.g., a prescribed motion). The movement unit may extend cantilevered from a movable member, a trigger, or both. The movement unit may extend into contact with a latch unit to form a locked state. The movement unit may move in relationship to the latch unit to form an unlocked state. The movement unit may move in a prescribed motion at all times and the latch unit may move relative to the movement unit so that a lockable state, an unlockable state, a locked state, an unlocked state, or a combination thereof may be formed. The movement unit may include one or more bar arms, one or more bars, or both.

The one or more bar arms may function to extend from a movable member so that a portion of the bar arm, the bar, or a combination thereof are extendable into or into contact with a ground member, a latch unit, an indictor mechanism, or a combination thereof. The one or more bar arms may extend cantilevered from the trigger, the movable member, or both. The one or more bar arms may extend partially into the latch unit, a latching pathway, around a hook latch, into contact with an indicator leg, past an indicator leg, or a combination thereof. The one or more bar arms may be located at virtually any location on a movable member, a trigger, or both. Preferably, the one or more bar arms are located on a bottom of the movable member. The one or more bar arms may be linear in shape. The one or more bar arms may be tapered. The one or more bar arms may include one or more contact elements (e.g., notches or bars). The bar arm may include one or more contact elements that contact the indicator leg to actuate the indicator leg. The one or more bar arms may taper as the bar arms extend away from the movable member and towards the ground member. The one or more bar arms may taper in shape so that once a sufficient amount of the bar arm extends into the latch unit, the latching pathway, or both the one or more bar arms may be prevented from extending further into the latch unit, the latching pathway, or both. A distal end, narrowest region, tapered portion, end that extends into the latch unit, end that extends into the latching pathway, or a combination thereof may include one or more bars, one or more contact elements, or both. If one or more notches are present, the one or more notches may be located on a different side or different edge of the bar arm than the bars. Preferably, the one or more bars may be located on a side of the bar arm. More preferably, the one or more bars extend substantially normal from the bar arm. The one or more bar arms may include one or more notches, one or more bars, one or more contact elements, or a combination thereof.

The one or more contact elements function to move into contact with one or more parts of the ground member to create a locked state, an indication, or both. The one or more contact elements may assist in locking the movable member to the ground member when the surgical device is in the lockable state. The one or more contact elements may be free of locking the ground member to the movable member when the surgical device is in the lockable state and a separate member (e.g., bar and hook latch) may connect together to form a locked state. The contact elements may contact the indicator mechanism, the tab, the indicator leg, or a combination thereof. Preferably, the contact element contacts the indicator leg to create a an indication. The contact element upon movement along the prescribed path may contact the indicator leg at substantially a same location in a forward stroke and a return stroke (e.g., within about 5 mm or less, about 3 mm or less, or about 2 mm or less). A contact location of the contact element may vary due to a thickness of the indicator leg, thus, on a forward stroke a first location may be contacted and on a return stroke a second location may be contacted that is different the first location. Hysteresis may affect the contact location on a forward stroke versus a return stroke so that the contact location or contact distance may vary (e.g., 5 mm or less, 3 mm or less, or preferably 1 mm or less). The contact distance may be a distance from a latching pathway to contact between a contact element and the indicator leg, the pocket, the entry apex, the exit apex, or a combination thereof. The contact distance on a forward stroke and a return stroke may be substantially a same location. The contact distance on a forward stroke and a return stroke may vary by about 5 mm or less, about 3 mm or less, about 1 mm or less, or about 0 mm or more. The contact location between the contact element and the indicator leg may have a substantially similar contact distance as contact between the bar and the entry apex, the pocket, the exit apex, or a combination thereof. The contact location may occur before a contact location with an entry apex, pocket, exit apex, or a combination thereof would occur so that the indication occurs at a same location as the bar contacts the pocket, entry apex, exit apex, or a combination thereof. For example, the contact element may contact the indicator leg and then move the indicator leg a distance before an indication is produced. The contact location plus the distance may be equal to a contact location between a bar and an entry apex, pocket, or exit apex so that the indication occurs where locking or unlocking may occur. The distance of indication may be a distance to compress a dome, move contacts into contact, or both. The distance may be about 0.5 mm or more, about 1 mm or more, about 2 mm or more, about 1 cm or less, or about 5 mm or less. The distance of indication (e.g., contact location plus a distance of movement) may be substantially equal to or behind where the bar contacts the pocket in the locked state so that an indication of a clamp force is indicated to a user, which suggests a desired clamp has been achieved when the surgical device is in the locked state. The contact distance in a locked state may be substantially equal to an indicator position when the latch unit is in the unlockable state. The contact element may be a bar, a notch, or both that contacts a hook latch, a pocket, an entry apex, an exit apex, an indicator leg, or a combination thereof.

The one or more notches may function to contact an indicator leg and bias the indicator leg so that an indication is formed. The one or more notches when moved into contact with the indicator leg may generate an indication without biasing the indicator leg. The one or more notches may bias the indicator leg. The one or more notches may be located at predetermined positions that each provide an indication. The notches may contact the indicator leg at a position indicating where a bar would contact a pocket. The one or more notches may be located between the trigger and a bar. The one or more notches may be "v" shaped, "L" shaped, "c" shaped, or a combination thereof. The one or more notches may be located at a distal end of the bar arm. The one or more notches may be located between a distal end and a proximal end of the bar arm. The one or more notches may connect to and temporarily move the indicator leg, the tab, or both. The one or more notches may move the indicator leg a predetermined distance and compress the dome and then release the indicator leg so that a subsequent notch may move the indicator leg. The one or more notches may move the indicator leg in both a first direction and a second direction. Preferably, the one or more notches only move the indicator leg a first direction. The one or more notches may be located in line with the bar so that the one or more notches indicator when a bar would be located within the pocket, move around the entry apex, move around the exit apex, or a combination thereof. The one or more notches may be located on an opposing side of the bar arm as the bar.

The one or more bars may function to connect the movement unit to the latch unit so that movement of the movable member relative to the ground member is prevented (e.g., create a locked state). The one or more bars may function to contact an indicator mechanism and preferably an indicator leg when the closure assembly is in the unlockable state. The one or more bars may move through a pathway in a forward stroke to connect to the latch unit or contact the indicator mechanism and then move through the pathway in a return stroke to release, move away from the latch unit, or move away from the indicator mechanism. The one or more bars may be virtually any shape so that the bars are movable through a latching pathway into the latch unit and then along a pathway to create a locked state and an unlocked state. The one or more bars may contact a hook latch to create a locked state. The one or more bars may contact an indicator leg to generate an indication. The one or more bars may be moved away from a hook latch or the indicator leg to move along the pathway from a locked state to an unlocked state (e.g., a return stroke) or from an indication state to a non-indication state respectively. The one or more bars may only extend along one side of the hook latch. Preferably, the one or more bars may circumnavigate the hook latch. The one or more bars may be a projection that extends from the bar arm and ultimately from a movable member or a trigger so that when the bar is trapped the movable member, the trigger, or both are prevented from being moved. The bar may be cylindrical, cubical, a cone, a cuboid, or a combination thereof. Preferably, the bar is cylindrical so that the bar may extend through a latching pathway, into the latch unit, and around a pathway of the latch unit.

The latching pathway may function to receive the bar into the latch unit the ground member, the housing, the handpiece, the handle, or a combination thereof. The latching pathway may extend along or include the prescribed path. The latching pathway may be an opening in the housing, hand piece, forceps, handle, or a combination thereof. The latching pathway is aligned with the bar so that as the bar moves in a prescribed motion the bar will pass into and through the latching pathway. The latching pathway may be an absence of material. The latching pathway may be part of the housing, handle, hand piece, or a combination thereof (e.g., a gap or spaced formed in the housing). The latching pathway may permit ingress and egress of the latch unit relative to the housing, the handle, hand piece, or a combination thereof.

The latch unit may function to create a connection with a movement unit so that the movable member and the ground member are locked together. The latch unit may include an indicator mechanism that functions to indicate a position of the movement unit relative to the latch unit. In the locked state, the bar is impeded from moving by the latch unit so that the trigger, movement member, or both cannot perform a return stroke. The latch unit may retain a portion of the movement unit. The latch unit may move as the movement unit moves along a prescribed path, an arcuate movement, or both. The latch unit may include a lockable state, an unlockable state, or both. In the unlockable state, the latch unit may be free of movement caused by the movement unit. In the unlockable state, the hook latch may be moved and all or a portion of the indicator mechanism may be moved into the prescribed path of the bar, the bar arm, the notch, or a combination thereof. The latch unit may be under a load (or pre-load) when the closure assembly is moved between or to a home position, a locking position, an unlocked position, a lockable state, an unlockable state, or a combination thereof. The latch unit may move along a longitudinal axis (e.g., all or a portion of the latch unit may move along the handle, the hand piece or both up and down as the movement unit moves into contact with the hook latch or out of contact with the hook latch). The latch unit may be in a pre-loaded state (e.g., a bias member may be a compression spring that is compressed) before the movement unit is in contact with the latch unit. The latch unit may be pre-loaded by a bias member being constrained between a forward bias constraint and rearward bias constraint.

The forward bias constraint may function to create one end of a constraint that places a load on a bias member so that the bias member is pre-loaded. A rearward bias constraint may function to create a second end of a constraint that places a load on a bias member so that the bias member is pre-loaded. The forward bias constraint, the rearward bias constraint, or both may be connected to the latch unit and preferably to the latch plate. The forward bias constraint and the rearward bias constraint (hereinafter bias constraints) may be connected to the latch plate and cause movement of the latch plate as the bias member is loaded and unloaded between the bias constraints. The bias constraints may form a box structure that extends along all sides of the bias member. The bias constraints may only extend along axial ends of the bias member. The bias constraints may extend along a forward end and a rear end of the bias member. The bias constraints may be a static member and may support one or more bias members as the forward movable bias constraint, rearward movable bias constraint, or both move, contact the bias member, or both. The bias constraints may be located below or adjacent to all or a portion of the indicator mechanism. The bias constraints may be a post, a wall, a contact surface, a contact surface including one or more guides, two contact surfaces that a separated by a guide, or a combination thereof. The forward bias constraint and the rearward bias constraint may be connected on a first side, a second side, or both by one or more side bias constraints.

The one or more side bias constraints may function to maintain a bias member within a plane, along an axis, all of the helical loops concentric to each other, or a combination thereof. The one or more side bias constraints may prevent bowing or bending of a bias member. The one or more side bias constraints may contact the bias member at one or more locations. The one or more side bias constraints may be a wall, an extension of the forward bias constraint, the rearward bias constraint, or both. Preferably, there are two side bias constraints and the two side bias constrains are parallel. The one or more side bias constraints may be connected to the latch plate. The one or more side bias constraints may be free of contact with the forward bias constraints, the rearward bias constraints, or both. Latch plate may be free of side bias constraints. The side bias constraints may support a selection plate, the indicator mechanism, or both. The one or more side bias constraints may extend parallel to a longitudinal axis of the bias member, parallel to a sliding axis of the forward movable bias constraint, rearward movable bias constraint, a latch plate, or a combination thereof.

The one or more forward movable bias constraint, one or more rearward movable bias constraints, or both (hereinafter movable bias constraint) may function to change a load on a bias member that is pre-loaded between two bias constraints. The movable bias constraints and the indicator mechanism may both be connected to a selection plate. The movable bias constraints may move relative to the bias constraints, the latch plate, or both. The movable bias constraints may move between a lockable state and an unlockable state. The movable bias constraints may change a load of the bias member as the latch plate moves along a sliding axis. The movable bias constraint when in a lockable position may be positioned so that as the latch plate moves along the sliding axis the load on the bias member is increased. The movable bias members may increase a load in the bias member when the latch plate moves in a first direction (e.g., rearward), in a second direction (e.g., forward), or both. Preferably, the movable bias members increase a load on the bias member, relative to the pre-load, when the latch plate moves in the first direction and the second direction. The forward movable bias member may be located at a forward end, proximate to a forward bias member, or both. The rearward movable bias member may be located at a rearward end, a rearward bias member, or both. The movable bias members may be a post, a wall, a contact surface, a contact surface including one or more guides, two contact surfaces that a separated by a guide, or a combination thereof.

The rear post and the forward post may function to pre-load a bias member. The rear post and forward post may be substantially aligned and a bias member may extend therebetween. The rear post and the forward post may be static relative to each other, the hook latch, the handle, the housing, the hand piece, or a combination thereof. The rear post and forward post may be movable relative to the housing, the handle, the hook latch, the hand piece, or a combination thereof. The rear post and the forward post may be movable between a lockable state and an unlockable state. The rear post and the forward post may contact a bias member and constrain the bias member therebetween to form a pre-load. The rear post, the forward post, or both may be connected to a latch plate. The rear post and the forward post may both be connected to a selection plate. The rear post, the forward post, or both may extend cantilever from the latch plate or the selection plate. A contact surface may be located on each side of the rear post, the forward post, or both and the rear post, the forward post, or both may extend between the one or more contact surfaces and the bias member may contact the contact surfaces. The rear post, the forward post, or both may be a contact surface that contacts the bias member when the rear post, the forward post, or both are connected to the selection plate. The rear post, the forward post, or both may be movable with the latch plate and may extend through a rear guide, a forward guide, or both respectively as the latch plate moves. The rear post, the forward post, or both may be static and the rear contact surface including a rear guide, a forward contact surface including a forward guide, or both may move to receive a rear post or a forward post respectively to bias the bias member. The rear post, the forward post, or both may taper from a base (e.g., a portion connected to the latch plate or the selection plate) toward a top end. taper of the rear post, the forward post, or both may extend at an angle of about 10 degrees or less, preferably about 5 degrees or less, or about 3 degrees or less relative to a line or plane normal to a surface of the latch plate or the selection plate. The taper of the rear post, the forward post, or both may extend at an angle of about 0.5 degrees or more, about 1 degree or more, or about 2 degrees or more relative to a line or plane normal to a surface of the latch plate or the selection plate. The rear post, the forward post, or both may assist in creating the pre-load when connected to the selection plate, or the latch plate. The rear post, the forward post, or both may be located proximate to or extend through a forward guide a rear guide, or both.

The guides may function to compress the bias member as the bias member moves along the longitudinal axis, a longitudinal axis of the bias member, or both. The guides may function to guide a post into contact with a bias member. The guides may function to allow a post to move between two contact surfaces. The guides may function to guide the posts longitudinally while contact surfaces on one or both sides of the guides contact the bias member so that the bias member is compressed. A rear guide may be located near a rear post and a forward guide may be located near a forward post. The forward guide may be located between the forward post and the hook latch. The forward guide may be part of a latch plate that is movable between a lockable state and an unlockable state. The guides may be located along a sliding axis, a longitudinal axis of the bias member, a longitudinal axis of the handle, or a combination thereof. The guides may be an absence of material that a post may extend through. The guide may be sufficiently small so that a bias member cannot extend through the guide. The guides may have a recess that permits the posts to extend a predetermined distance and once the posts reach the end of the recess the posts may be prevented from traveling further. A contact surface may be located on one or both sides of the guides and the bias device may contact the contact surfaces as the posts travel into the guide and the contact surfaces may restrict travel of the posts, the latch plate, or both while compressing the bias member.

The rear contact surface and the forward contact surface (hereinafter contact surfaces) may function to assist in compressing the bias member (e.g., a spring) as the latch plate, the selection plate, or both move. The contact surface may be a portion of a wall that a bias member contacts. The contact surfaces may be a shoulder located on each side of the guide. The contact surfaces may be located proximate to the rear post, the forward post, or both so that as the post extends into a rear guide or the forward guide, the bias member contacts the rear contact surface or the forward contact surface respectively. The contact surfaces may be part of the selection plate, the latch plate, or both and the contact surfaces may impart all or a portion of a pre-load on a bias member. The contact surfaces may have a taper. The contact surfaces may have a taper angle. The taper of the contact surface may be such that the contact surface gradually increases in distance from a bias member as the contact surface extends from a base to a top end. The contact surfaces may be part of the selection plate, the latch plate, or both and the location of the contact surfaces relative to the bias member, the posts, or both may be moved by moving the selection plate.

The selection plate may function to change the closure assembly between a lockable state and an unlockable state. The selection plate may move along a sliding axis to activate and deactivate the closure assembly (e.g., change the latch unit between a lockable state and an unlockable state). The selection plate may move so that the one or more posts the bias member, or both are moved from a contact state (e.g., lockable state) to a non-contact state (e.g., unlockable state) with the guides. The selection plate may allow a user to enable and disable the closure assembly. The selection plate may be substantially entirely located within the housing, hand piece, handle, or a combination thereof. The selection plate may include a rear post, a rear cross bar, a forward post, a forward cross bar a hook latch, a wall guide, one or more walls with one or more contact surfaces, a rear guide in a wall with a contact surface, a forward guide in a wall with a contact surface, an indicator mechanism, or a combination thereof. The selection plate may include a forward guide, a rear guide, an adjustment switch, a contact surface, or a combination thereof. The indicator mechanism may be connected to the selection plate so that when the selection plate is moved from a lockable state to an unlockable state, the indicator mechanism is moved into the predetermined path. The indicator mechanism may have a portion that extends from the selection plate and extend off of the selection plate. The selection plate may include an adjustment switch that extends out of the housing, hand piece, handle, or a combination thereof an is exposed for movement by the user.

The adjustment switch may function to move the closure assembly, deactivate the closure assembly, activate the closure assembly, or a combination thereof. The adjustment switch may be exposed so that upon a force being applied to the adjustment switch the state of the closure assembly is changed. The adjustment switch may be a thumb switch. The adjustment switch may include one or more gripping portions. The adjustment switch may house all or a portion of an indicator mechanism. The adjustment switch may include one or more indicator apertures. The tab, bias tab, done, contact leg, body, a portion of the indicator leg, or a combination thereof may be located within the adjustment switch. A portion of the indicator mechanism may extend through the indicator apertures so that the indicator mechanism extends into a prescribed path of the bar, the bar arm, or both. Preferably, the indicator leg extends our of the adjustment switch through the indicator aperture. The adjustment switch may be movable along a switch path. The switch path may be parallel to the sliding axis. The adjustment switch may move the selection plate so that a detent pin is moved between the unlockable state detent and the lockable state detent to change the function of the closure assembly (e.g., activate and deactivate).

The unlockable state detent functions to lock the latch plate in an unlockable state to allow free movement of the movable member and the ground member relative to each other by locking the position of the latch unit out of the path of the movement unit. The unlockable state detent functions to lock the latch plate, the hook latch, or both out of alignment with the bar, the closure assembly, or both so that a lockable state is not created. The lockable state detent functions to lock the latch plate in a lockable state so that the latch plate assists in restricting movement of the movable member and the ground member relative to each other by locking the position of the latch unit, the latch plate, the hook latch, or a combination thereof in the path of the movement unit. The unlockable state detent and the lockable state detent (hereinafter detents) may lock the selection plate, the latch plate, or both in a lockable state or an unlockable state. The detents may be a recess that receives a pin or a pin that extends into a recess. The detents may prevent movement once a state is selected. The detents may be located on one or both sides of the selection state. Preferably, each side of the selection plate includes at least two detents. The detents may move the indicator mechanism in and out of alignment with the bar, bar arm, or both. For example, when the unlockable state detent is in use the indicator mechanism may be aligned with the prescribed path and when the lockable state detent is in use the indicator mechanism may be located out of the prescribed path so that the indicator mechanism is not contacted. The detents may positively receive a pin. The detents may be sinusoidal in shape. The detents may have two or more valleys and each valley may be separated by a peak. Preferably, the detents include at least three peaks with a valley between the three peaks forming a lockable state detent and an unlockable state detent. Once the detent pin gets over the peak the pin may fall into a valley and lock.

The detent pin functions to create a locked state, an unlocked state, or both with the closure assembly. The detent pin functions to contact a detent and then lock the selection plate in a selected location. The detent pin may be a projection that extends into and is received by the detent. The detent pin may ground (e.g., prevent movement of) the closure assembly, the latch unit, the selection plate, or a combination thereof. The one or more detents may act as a stop; however, the closure assembly may include a rear stop, a forward stop, or both to constrain movement of the selection plate relative to the latch plate or vice versa.

The forward stop, the rear stop, or both (hereinafter stops) may function to prevent the selection plate, the latch plate, the indicator mechanism, or a combination thereof from being moved out of axial alignment, the bias member from being over constrained, the bias member from being moved off of the rear post, rear crossbar, forward post, forward cross bar, or a combination thereof. The stops may be a back up to the detents to prevent movement of the selection plate beyond the detents. The stops may be an emergency stop in an event of failure of a detent. The stops may be part of the latch plate or the housing so that the selection plate may remain constrained within a predetermined location relative to the latch plate, the housing, or both.

The one or more latch plates may function to move when a hook latch is contacted by a bar so that a locked state, an unlocked state, or both are created. The one or more latch plates may function to move when the hook latch is positioned in the prescribed path of the bar, along a forward stroke, a return stroke, or a combination thereof. The latch plate may carry one or more elements that form the pathway. The latch plate may carry the posts, the bias member, the hook latch, the wall guide, all or a portion of the indicator mechanism, or a combination thereof. The latch plate may be generally static and then movable once acted upon by the movement unit. The latch plate may only move when the latch unit is in a lockable state (e.g., during locking or unlocking of the closure assembly or moving the closure assembly between a lockable state and an unlockable state). The latch plate may only move when contacted by the movement unit. The latch plate may move along the sliding axis, tracks, the hand piece, the housing, or a combination thereof. The latch plate may move without moving the indicator mechanism. The indicator mechanism, selection plate, or both may be static relative to the latch plate when the closure assembly is in the lockable state. The latch plate may move along one or more tracks in or along the housing.

The tracks may function to guide the latch plate, the selection plate, or both parallel to the sliding axis. The one or more tracks may function to movably connect the latch plate to the selection plate. The tracks function to assist the latch plate is moving along a predetermined path. The tracks assist the latch plate in moving along an axis. The tracks may be protrusions in the housing that extend into contact with the latch plate. The tracks may be one or more raised surfaces that the latch plate moves along. A track may be on a first side, a second side, or both sides of a latch plate, a selection plate, or both. Preferably, the latch plate or the selection plate includes four tracks (e.g., two on each side). The one or more tracks may prevent the latch plate and the selection plate from being separated as the latch plate and selection plate move relative to each other. The one or more tracks may move along rails or vice versa. The one or more tracks may prevent movement of the latch plate normal to the selection plate. The one or more tracks, one or more rails, or both may assist in maintaining alignment of the indicator mechanism so that the indicator mechanism aligns with the prescribed path when the closure assembly is in the unlockable state. The one or more tracks may slide over the rails to create a connection.

The one or more rails may function to connect the latch plate to the selection plate. The one or more rails may work in conjunction with the tracks. The one or more rails may guide the tracks during movement. The one or more rails when coupled to the tracks may prevent orthogonal movement or normal movement of the latch plate to the selection plate. A rail may be on a first side, a second side, or both sides of a latch plate, a selection plate, or both. Preferably, the latch plate or the selection plate includes four rails (e.g., two on each side). The rails may allow for longitudinal movement and prevent movement in a direction other than the longitudinal movement. The one or more rails and tracks may assist in pre-loading or maintaining a pre-load of the bias member, loading the bias member, or both.

The bias member may function to store energy when a force is applied to the latch plate and then to the energy when the force is removed. The bias member may function to move the latch plate back towards home position. The bias member may assist in locking or unlocking the movable member and the ground member. The bias member may be any material that may store energy. The bias member may be elastomeric, rubber, a spring steel, helical, round, cylindrical, or a combination thereof. Preferably, the bias member is a compression spring that stores and releases energy. The bias member when located within the latch unit and the latch unit being in a home position may have a pre-load. The pre-load may be changed by movement of the selection plate, the latch plate, or both. The change in load may be sufficiently large so that the bias member returns the latch unit back to the home position when the latch unit moves from a locked state to an unlocked state, in an unlockable state, a lockable state when the hook latch is not biased, or a combination thereof. The bias member may be a double acting bias member. The bias member may bias towards the home position regardless of whether the bias member is biased in a first direction or a second direction. The bias member may be compressed when the hook latch is contacted by the bar.

The hook latch may function to create the locked state. The hook latch may function to catch the bar and prevent movement of the movable member relative to the ground member. The hook latch may have two sides or more, three sides or more, or four sides or more. The hook latch may have a first side (e.g., an entry portion) that assists in creating a locked state. The hook latch may have a second side (e.g., a return portion) that assist in retaining a bar so that the locked state is maintained. The hook latch may have a third side that assists in creating an unlocked state. The hook latch may include an angled portion, a linear portion, an entry apex, entry portion, exit portion, exit apex, pocket, or a combination thereof.

The one or more entry portions may function to assist in creating a locked state when the bar contacts the entry portions. All or a portion of the one or more entry portions extend across the latching pathway when the selection plate is in the lockable state. The entry portion may be angled so that as the bar traverses along the prescribed motion the bar is moved towards the entry apex and ultimately the pocket. The latch plate may continue to move as the bar travels along the entry portion until the bar reaches the entry apex. The entry portion may terminate at an entry apex.

The entry apex may function to assist the bar in entering the pocket. The entry apex may prevent the bar from exiting the pocket from a same direction the bar entered the pocket. The entry apex and an exit apex may be located on opposing sides of the pocket.

The pocket may function to receive the bar so that a locked state is formed. The pocket may be a wall that the bar is biased against so that the bar is restricted from being moved back into the latching pathway. The pocket and the indicator mechanism, indicator leg, or both may be coplanar, collinear, or both. The pocket and indicator mechanism, indicator leg, or both may be located in different planes, different lines, or both. The pocket may be a recess that the bar resides within so that the locked state is formed and the bar is not inadvertently moved out of the pocket. The pocket may resist a biasing force of the movable member away from the ground member. The pocket may prevent longitudinal movement of the bar. The exit apex, the entry apex, or both may extend beyond the pocket so that the bar remains within the pocket until a bias force of the movable member is resisted, a user regrips the movable member and the ground member together, or both. Upon regripping, resisting a bias force or both the bar may exit the pocket by extending around the exit apex.

The exit apex may function to prevent a bar from inadvertently exiting the pocket. The exit apex may extend beyond the pocket. The exit apex may be a point that once the bar extends beyond the bar cannot reenter the pocket. The bar may contact the exit apex while exiting so that the latch plate is biased, and upon the bar stopping contact with the exit apex, the latch plate may bias away from the bar so that the prescribed motion of the bar is above the pocket and the bar cannot reenter the pocket. The exit apex may be formed between the pocket and the return portion.

The return portion may function to guide the bar from the locked state to an unlocked state. The return portion may function to guide the bar to the latching pathway. The return portion may be located above the latch plate when the latch plate is in the home position. For example, the hook latch may block the latching pathway when the latch plate is in the home position, and as the bar moves along a prescribed path the bar may contact the return portion of the hook latch and move the hook latch to open the latching pathway. As the latching pathway is being opened the bias device may be compresses an energy stored within the bias device. Once the bar stops contacting the return portion (e.g., leaves the pathway) and reenters the latching pathway the bias device may bias the latch plate back to a home position.

The pathway may function to guide the bar from a home position to a locked position, from a locked position to an unlocked position, from an unlocked position to a home position, or a combination thereof. The pathway may assist a bar in circumnavigating a hook latch. The pathway may be tortuous. The pathway may be a labyrinth. The pathway may be an open area in the movement unit that the bar is guided through. The pathway may extend along an entry portion, along a return portion, around an entry apex, into a pocket, around an exit apex, into a wall guide, around a guide apex, around a release apex, along a rear wall, or a combination thereof. The pathway may permit the bar to move around the release apex of the hook latch, move into contact with the wall guide, or both.

The release apex may function to guide the bar into the pathway and out of the pathway. The release apex may align an entry end of the pathway with the latching pathway when the latch unit is in the locked state. The release apex may align an exit end of the pathway with the latching pathway when the latch unit is in the locked state. The release apex may move from a first side of a latching pathway to a second side of a latching pathway. The release apex may connect the pathway to the latching pathway. The release apex may form a point of the hook latch. The release apex may be a beginning and end of the hook latch. The release apex may be located opposite the pocket. The release apex may be located opposite the wall guide.

The one or more wall guides may function to assist the bar in moving from a locked position to an unlocked position, an unlocked position to a locked position, or both. The one or more wall guides may restrict movement in a first direction (e.g., vertically, towards a forward post), in a vertical direction, or both when the bar is moving from an unlocked position to a locked position. The one or more wall guides may include a guide apex that extends towards the pocket, towards the hook latch, or both.

The one or more guide apexes may function to prevent the bar from moving through the pocket without a locking state being formed, without the bar being in the locked position, or both. The guide apex may be located between the entry apex and the exit apex. The guide apex may connect to the wall and the rear wall may connect the guide apex to the wall.

The rear wall may function to guide the bar around the exit apex. The rear wall may extend at an angle relative to the guide apex. The rear wall may guide the bar as the bar moves along a prescribed motion, an arcuate movement, or both.

The arcuate movement may function to move the bar from a home position, to a locked position, to an unlocked position, to an indicator position, or a combination thereof. The arcuate movement may be a movement of the bar, the trigger, a movable member, or a combination thereof as the bar, the trigger, a movable member, or a combination thereof rotate about a pivot. The arcuate movement may be a prescribed movement of the bar, the trigger, the movable member, or a combination thereof. The arcuate movement may be the only movement the trigger, the bar, the movable member, or a combination thereof makes. The arcuate movement may move the bar from a home position to a locking position, a locking position to an unlocked position, and an unlocked position back to a home position. The arcuate movement may move the bar into contact with an indicator mechanism.

The one or more indicator mechanisms may function to indicate when the closure assembly, bar, bar arm, or a combination thereof are in a locked position (e.g., a position where the closure assembly would be in a locked state); unlocked position; full pull position; partial pull position; or a combination thereof. The indicator mechanism may indicate one or more positions of the movable member relative to the ground member. The one or more indicator mechanism may indicate a position of a bar, a bar arm, or both relative to the hook latch, the wall guide, or both. The indicator mechanism may be monostable. The indicator mechanism may move back to a home position after the contact element moves the indicator mechanism, indicator leg, or both. The one or more indicator mechanism may provide an indicate when the closure assembly is in the lockable state, the unlockable state, or both. Preferably, the one or more indicator mechanisms provide an indication only when the closure assembly is in the unlockable state. More preferably, the indicator mechanism indicates when a bar would be located within a pocket, extending around the entry apex, or both when the closure assembly, the selection plate, or both are in the unlockable state. The indicator mechanism may include one or more tabs that extend from the indicator mechanism, the selection plate, the adjustment switch, or a combination thereof.

The one or more tabs may function to extend from the indicator mechanism into the prescribed path. The one or more tabs may be movable along the prescribed path. The one or more tabs may physically create an indication (e.g., audible, haptic, visual, or a combination thereof). All or a portion of the tabs may be movable relative to the selection plate, the adjustment switch, or both. A portion of the tab may be static relative to the selection plate, the adjustment switch, or both. The one or more tabs may extend along a plane that is coplanar with the pocket, or parallel to a pocket by located in front of the pocket so that when the tab is moved the tab provided an indication of a location of the pocket, the entry apex, the exit apex, or a combination thereof. The one or more tabs may extend from the selection plate, the latch plate, or both. An entire length of the tab, the indicator leg, or both may be located within a single plane that is coplanar with or parallel to the pocket. The tab, the indicator leg, or both may extend at an angle relative to a plane of the pocket. The one or more tabs may electrically create an indication. The one or more tabs may move one or more parts so that the indication is produced when the parts are moved a predetermined distance. The one or more tabs may create a circuit, close a circuit, or both when the tab is moved a predetermined distance. The one or more tabs may create resistance as the movable member is moved relative to the ground member so that a user feels the increase in resistance. The one or more tabs may be in contact with or connected to one or more domes. The one or more tabs may contact the one or more domes as the one or more tabs are moved. The one or more tabs may deflect the dome, move the dome into contact with another part to complete a circuit, or both. The one or more tabs may have a portion that extends out of an indicator aperture in the adjustment switch. A portion of the tab may be located within the adjustment switch and a portion of the tab may extend out of the adjustment switch. The tab may extend along a single plane. The tab may extend within two or more planes. The tab may include a bias tab and a tab that are connected together to form the tab.

The bias tab may function to move the tab back to a home position when the tab is biased. The bias tabs may connect the tab to the selection plate, the adjustment switch, or both. The bias tab may remain substantially static relative to the adjustment switch, the selection plate, or both. The bias tab may be connected to the adjustment switch so that the bias tab is not movable relative to the adjustment switch. The bias tab may extend at an angle relative to the indicator leg. The bias tab may extend into a connection finger, contact a connection finger, or both. The bias tab may store energy so that once the bar, bar arm, or both are free of contact with the tab, the bias tab may move an indicator leg back to a home position. An angle between the bias tab and indicator leg may be decreased as the tab is biased so that energy is stored between the bias tab and the indicator leg. The bias tab, the material connecting the bias tab and the indicator leg, or both may store energy that moved the indicator leg after the indicator leg is biased. The angle between the bias tab and the indicator leg is increased as the tab is biased so that energy is stored between the bias tab and the indicator leg.

The indicator leg may function to be contacted by the bar, the bar arm, or both and indicate a position of the bar, indicate a position of the movable member when the movable member is in the lockable state, the unlockable state, or both. The indicator leg may be partially located within the adjustment switch. The indicator leg may extend out of the adjustment switch through an indicator aperture. The indicator leg may be straight, bent, include one or more curves, one or more supports, or both. The indicator leg may curve downward towards the latch plate, into contact with the latch plate, above the latch plate, towards the latch plate, or a combination thereof. The indicator leg may extend outward into the prescribed path. The indicator leg may be sufficiently long so that when the latch plate is in the unlockable state the indicator leg is located within the prescribed path. The indicator leg may be sufficiently short so that when the latch plate is in the lockable state the indicator leg is located out of the prescribed path. The indicator leg, tab, bias tab, connection between the bias tab and the indicator leg, or a combination thereof may be made of any material that may be flexed, moved, create an electrical connection, compress a dome, elastically deform, store energy, or a combination thereof. The indicator leg may extend at an angle relative to the pocket so that once the indicator leg is moved to be substantially coplanar with the pocket an indication is created. The angle may be equal to a distance needed to create an indication. The distance may be about 0.5 mm or more, about 1 mm or more, about 2 mm or more, about 1 cm or less, or about 5 mm or less. The indicator leg, tab, bias tab, connection between the bias tab and the indicator leg, or a combination thereof may be made of or include metal, plastic, an electrically conductive polymer, spring steel, iron, copper, stainless steel, surgical steel, an elastomer, or a combination thereof. The indicator leg and the bias tab may be formed form multiple pieces of material and connected together. The indicator leg and bias tab may be formed of a single piece of material and then shaped. The tab may be stamped, cut, bent, or a combination thereof to form the indicator leg, bias tab, or both. The indicator leg may be sufficiently rigid so that as the indicator leg is moved by the bar, the bar arm, or both the dome is moved, compressed, a connection is formed (e.g., a circuit is closed), a light is illuminated, a noise is created, a haptic response is created, or a combination thereof.

The dome may function to create an audible signal, a visual signal, a haptic signal, or a combination thereof. The dome may be compressible, movable, elastically deformable, or a combination thereof. The dome may be sandwiched between one or more parts of the indicator mechanism. The dome may be located between the finger and the indicator leg. The dome may be connected to the finger, the indicator leg, or both. The dome may be static relative to the finger or the indicator leg. The dome may be movable relative to the finger or the indicator leg. The dome may be compressible. The dome may be generally hemispherical. The dome may have a concave side that faces the indicator leg and a convex portion that faces the finger or vice versa. The convex portion may be moved into contact with the finger when the indicator leg is moved by the bar, the bar arm, or both. The convex portion may deform, compress, snap, make a sound, close a circuit, or a combination thereof. The dome may have one or more contact legs that support the dome in a second plane, in a plane above the indicator leg, a plane above the indicator leg, or a combination thereof.

The one or more contact legs function to support the dome on or above the indicator leg. The one or more contact legs may function to elevate the dome above the contact leg. The one or more contact legs may move as the indicator leg is moved. The one or more contact legs may be a plurality of contact legs. The one or more contact legs may connect the dome to the indicator leg. The one or more contact legs may be immovable. The one or more contact legs may be one continuous leg that extends around a periphery of the dome. The one or more contact legs may connect the dome to the indicator leg so that the dome moves with the indicator leg. The one or more contact legs may elevate the dome so that the dome may be deformed. The one or more contact legs may be connected together by a body.

The body may function to deflect, make an indication, close a circuit, or a combination thereof. The body may be convex on one side and concave on an opposing side. The body may be movable inward towards the indicator leg. The body may extend into contact with a finger so that the finger deflects the body when the indicator leg is moved by the bar, the bar arm, or both. The body may be movable relate to the indicator leg, the finger, or both. The body may be generally round, dome shaped, hemispherical, or a combination thereof. The body may extend inward. The body may move into contact with a relay, an electrical contact, or both. The body may be electrically conductive to complete a circuit. The body may be in contact with a finger that biases the dome to create an indication.

The one or more fingers may function to bias the dome to create an indication. The one or more fingers may function to deflect the dome, press against the dome (directly or indirectly), or a combination thereof. The finger may be a static member of the selection plate. The finger may be a fulcrum. The finger may be located on one side of the indicator leg. The fingers may be located on two sides of the indicator leg. The dome may be sandwiched between the indicator leg and the finger. The fingers may have a shape that is square, round, oval, half circular, or a combination thereof. The fingers may project outward from the selection plate. The fingers may extend into a gap. The fingers may extend into an open space. The fingers may extend into a space of the indicator aperture. The fingers may be located adjacent to the connection finger.

The one or more connection fingers may function to retain the tab in place. The one or more connection fingers may function to hold the bias tab. The one or more connection fingers may prevent the bias tab from moving and allow the indicator leg to move. The one or more connection fingers may retain the bias tab in place, in the indicator aperture, or both. The one or more connection fingers may be flat, have one or more flat walls, have one or more angular walls, be circular, hemispherical, triangular, or a combination thereof. The connection fingers may prevent the tab from moving, being removed from the indication aperture, or both.

The indication aperture functions to support the tab, the indicator leg, or both as the indicator leg extends outward from the adjustment switch, into the prescribed path, or both. The indication aperture may constrain the tab, the indicator leg, or both so that when the indicator leg is biased the indicator leg elastically deforms, maintains contact with the bar, the bar arm, or both, is biased back to a home position, or a combination thereof. The one or more indicator apertures may prevent the bias tab from being removed from the adjustment switch. The one or more indicator apertures may support the indicator leg as the indicator leg extends cantilever from the adjustment switch. The one or more indicator apertures may create a fulcrum so that when the indicator leg is biased the indicator leg moves back to a home position without intervening force from the bar, bar arm, or both. The indicator aperture may be free of contact with the indicator leg in the home position, the deflected position, or both.

The home position may be a position of the bar when the bar is not located within the handle, the latch unit, the housing, the hand piece, or a combination thereof. The home position may be a position where the latch plate is at steady state, the bar is not within the latch unit, or both. The home position may be a position where the bias member is pre-compressed but the latch unit is not being biased. The latch plate may move from a locked position to a home position or vice versa, an unlocked position to a home position or vice versa, or both. The home position may be where the hook latch crosses the latching pathway. The home position may be where the bias member, the indicator mechanism, or both returns the latch plate upon an engagement force or a disengagement force being removed. The home position may be where the movement unit and the latch unit are disconnected, can move relative to each other, or both. The bar may move from an unlocked position, a locked position, an indicator position, or a combination thereof to a home position. The bar may move from a locking position to an unlocking position and then to a home position. The bar may move from a home position into contact with the indicator, the indicator leg, or both where the bar is in an indicator position.

The indicator position may be any position where all or a portion of the tab is located within the prescribed path; the bar, notch, or both is aligned with the indicator; or both. The indicator position and the unlockable position may be the same position. The indicator position may be where the indicator may provide an indication to a user the relative position of the bar, the bar arm, or both relative one or more parts of the hook latch, movable member, handle, or a combination thereof. The indicator position may be where the selection plate is moved from a lockable state to an unlockable state. The indicator position may indicate where a locking position of the closure assembly would be if the closure assembly was in the lockable state instead of the unlockable state.

The locking position may be where the bar is located within the pocket and the bar is prevented from moving by the hook latch. The locking position may be where the bar is located between the entry apex and the exit apex (i.e., within the pocket). In the locking position, the bar may bias the hook latch up or in a first direction (i.e., towards a forward post) as the bar enters the pathway. In the locking position, the bar may bias the hook latch down or in a second direction, which is opposite the first direction (i.e., towards a rear post) as the bar exits the pathway. In the locking position, the hook latch may be moved by the bar as the bar moved along the arcuate movement, the pathway, or both. The locking position may be located between two unlocked positions.

The unlocked position may function to allow the bar to move within the pathway. The unlocked position may function to move the hook latch, latch plate, or both out of alignment with the bar, the latching pathway, or both. The unlocked position may be any position where the bar is within the pathway but not located within the pocket. The unlocked position may be a bar in the pathway moving along the entry portion, the return portion, or both. The unlocked position may be where the bar is not located between the entry apex and the exit apex. The unlocked position may be where the latch plate, hook latch, or both are locked out of the prescribed motion, the arcuate movement, or both of the movement unit, the bar, or both. In the unlocked position, the hook latch may be locked out of alignment with the latching pathway, the arcuate movement, the prescribed motion, or a combination thereof of the bar. In the unlocked position, the latch plate may be in the unlocking state detent. In the unlocked state, the bar may be aligned with the indicator mechanism. The bar may be in the unlocked state when the latch plate may be in an unlockable state so that the bar is free to move into contact with the indicator mechanism. The bar may make a locking movement so that the bar changes from an unlocked position to a locked position.

The locking movement may be where the bar extends from an unlocked position to a locked position. The locking movement may be where the bar extends around an entry apex. The locking movement may be where the bar moves into contact with the guide apex and then upon release of the trigger, the movable member, or both the bar is moved into the pocket, from the guide apex into the pocket, into contact with the exit apex but retained in the pocket, or a combination thereof. The bar may make a locking movement, when the latch unit is in the unlockable state, and then contact the indicator mechanism and preferably the indicator leg to indicate a position of bar so that a locking position of the bar when in the pocket is indicated. The locking movement may be where the bar enters the pocket. The locking movement may be followed by an unlocking movement where the bar is released from the pocket.

The unlocking movement may function to release the bar from the pocket. The unlocking movement may be a movement around the exit apex. The unlocking movement may be a movement from the pocket to the wall guide where the wall guide assists in moving the bar around the exit apex, to a location above the exit apex, or both. The unlocking movement may extend away from the hook latch and then back towards the hook latch once the bar is above the exit apex. The unlocking movement may result in the bar being un an unlocked state. The unlocking movement may be where the bar moves out of the ground member even when the closure assembly is in the unlockable state. An unlocking movement may move the selection plate between a lockable state and an unlockable state.

The unlockable state may function to prevent the closure assembly from being locked. The unlockable state may be a state where the latch unit is configured to be out of a movement path of the movement unit so that a locked state cannot be formed. The unlockable state may be where the latch unit is moved to a second position where the latch unit and the movement unit are not aligned. The unlockable state may be where the hook latch is misaligned with the latching pathway so that as a bar extends into the latching pathway the bar and hook latch do not contact each other. In the unlockable state, the hook latch may be located entirely above or below the latching pathway. In the unlockable state the hook latch may be moved out of alignment and the indicator mechanism may be moved into alignment. The unlockable state may be where the indicator mechanism is moved into alignment with the prescribed path so that the bar, the bar arm, a notch, or a combination thereof contact the indicator mechanism, the indicator leg, or both. The unlockable state may be a state where the detent pin is located within the unlockable state detent. When the selection plate is moved from the unlockable state detent to the lockable state detent the closure assembly may change from the unlockable state to the lockable state.

The lockable state may function to allow the closure assembly to be latched. The lockable state may be a state where the movement unit and the latch unit are aligned and may connect together, may lock a movable member to a ground member, or both. In the lockable state, the indicator mechanism may be misaligned with the bar, the bar arm, the latching pathway, or a combination thereof. In the lockable state, the bar, bar arm, notch, or a combination thereof may be free of contact with the indicator mechanism. The lockable state may be where a portion of the hook latch is aligned with the latching pathway so that as a bar extends through the latching pathway the bar can contact the hook latch to create a locked state. The closure assembly, in the lockable state may have an unlocked state or a locked state. The unlocked state, of the lockable state, may be where the movable member and the ground member are movable relative to each other. The locked state, of the lockable state, may be where the movable member and the ground member are connected together. The latch unit may in a lockable state and changed between a locking state and an unlocking state, the bar may be movable between a locking state and an unlocking state, or both.

The locking state may function to lock the movable member and the ground member together. The locking state may be where the closure assembly is locked. The locking state may be where the latch plate is restricted from moving about a sliding axis by the bar.

The sliding axis may function to be an axis that the latch plate moves along from a first position to a second position, along the track, up and down, parallel to a length of the handle, or a combination thereof. As the latch plate moves along the sliding axis, compression of the bias member may be increased, decreased, or a combination of both. The as the bar moves along the hook latch, an engaging force may be applied to the hook latch that moves the latch plate along the sliding axis.

The engaging force may function to move the latch plate along the sliding axis, to compress the bias member, to lock the closure assembly, to lock the movement unit to the latch unit, create an indication, or a combination thereof. The engaging force may be sufficiently large to move the latch plate as the bias member compresses, move an indicator mechanism, move an indicator leg, compress a dome, or a combination thereof. The engaging force may increase as the bar moves along the hook latch. The engaging force may be created by a user. The engaging force may increase as the bar moves from the release apex towards the entry apex. The engaging force may increase as the bar moves along the return portion. The engaging force may increase as the bar moves from the exit apex to the release apex. Preferably, the engaging force is along a first side of the hook latch, along the entry portion, or both as the bar extends from the latching pathway and the pathway and into the pocket. The engaging force may be a single force that is generated by a user as the bar moves along a prescribed movement an arcuate movement, or both. The user may generate the engaging force by moving the movable member and the ground member towards each other. The engaging force may move an indicator leg. The engaging force may move the indicator leg so that a haptic signal is created, a noise, a dome is compressed, an indicator is moved, an indicator is biased, a circuit is closed, a circuit is broken, move all or a portion of the indicator mechanism in a first direction, or a combination thereof. The engaging force may be substantially similar to an amount of force required for a disengaging force.

The disengaging force may function to move the bar out of the pocket, around the exit apex, reverse an indication, release a portion of the indicator mechanism, or a combination thereof. The disengaging force may extend parallel to the engaging force. The disengaging force may have one or more forces along one or more different directions, vectors, or both. The disengaging force may remove a bar from the pocket and then remove the bar from the latch unit, the housing, the handle, the hand piece, or a combination thereof. The disengaging force may have a force component that is along the exit apex, along the wall guide, along the return portion, or a combination thereof. The disengaging force may be created by a user, a spring, a biasing member, or a combination thereof. The disengaging force may extend in the first direction and then the second direction. The disengaging force may only extend in the second direction. The disengaging force may be created by a regripping and movement of the movable member relative to the ground member. The disengaging force may first extend away from the hook latch, then up the rear wall, around the exit apex, and then along the return portion where the latch plate is moved along the sliding axis. Once the bar, movement unit, or both are released, the bar, movement unit, or both may change from a first disengagement force to a second disengagement force. The second disengagement force may move the latch plate along the sliding axis so that the bar is aligned with the latching pathway. The second disengagement force may be sufficiently large to compress the bias member. The second disengagement force may increase as the bar moves along the prescribed motion, the arcuate movement or both. The second disengaging force may move the indicator mechanism from an indicating position to an off position or a home position (e.g., a position where no indication is being created). The second disengagement force may move the latch plate from a home position to an unlocked position where the bar may separate from the latch unit.

In FIG. 1, the electrosurgical device 2 is shown including a handpiece 4 and forceps 10. The forceps 10 include a first working arm 20 and a second working arm 22. The handpiece 4 includes a housing 8 and a closure assembly 32 that prevents movement of the first working arm 20 and the second working arm 22 by locking the movable member 12 and the adjacent member 14 in a position. The movable member 12 is a trigger 24 and the adjacent member 14 is a handle 26. The forceps 10 are connected to the handpiece 4 by a stylet 6.

Figure 2A:
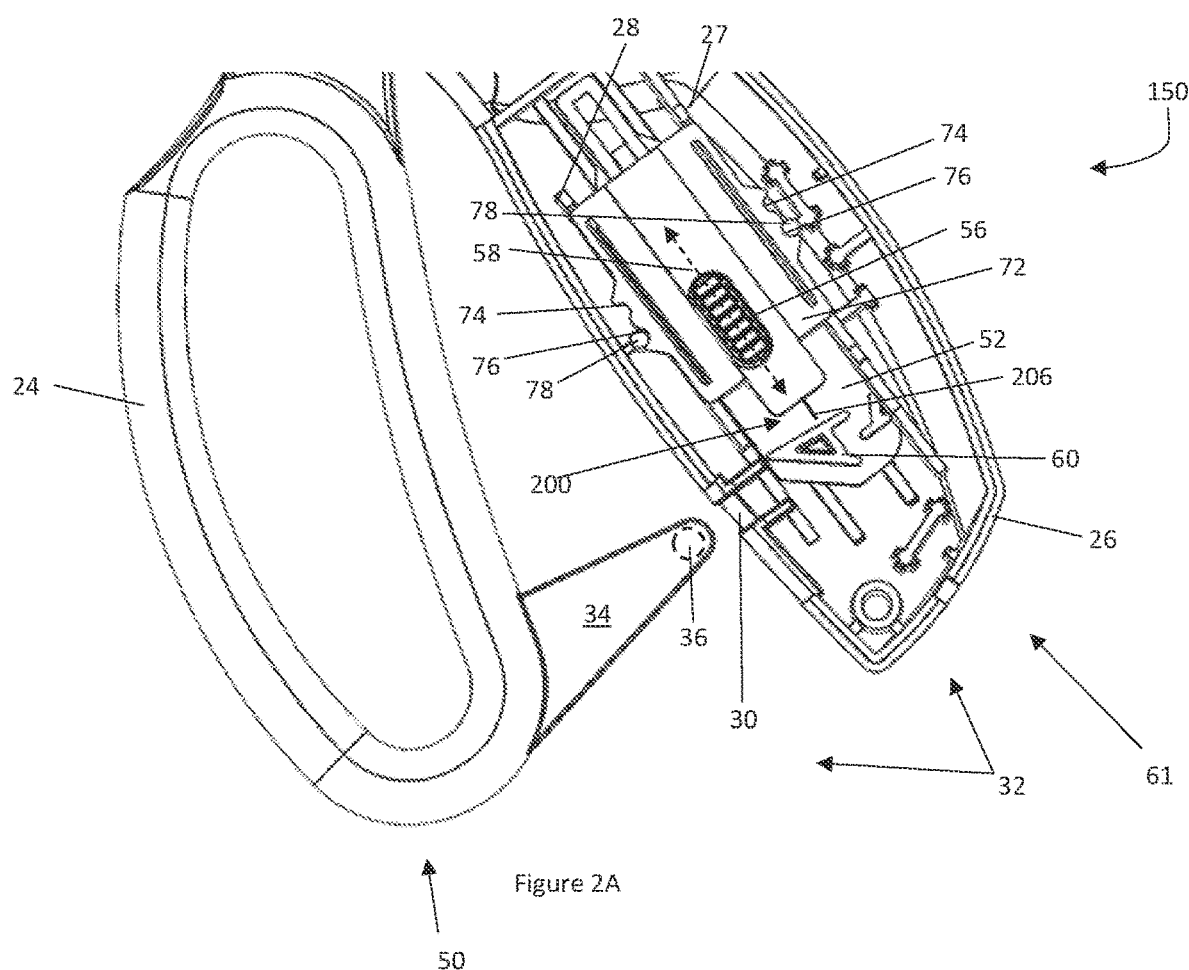
FIG. 2A illustrates a laterally bisected view of a closure assembly.

In FIG. 2A, a closure assembly 32 includes a movement unit 50 and a latch unit 61. The closure assembly 32 shows the trigger 24 and a selection plate 72 in a locking state 150. An indicator leg 206 protrudes from the selection plate 72. The trigger 24 includes a bar arm 34 to which a bar 36 is attached. The bar 36 is configured to pass through a latching pathway 30 in the handle 26. In the locking state 150, the bar 36 is aligned with and configured to contact a hook latch 60, which is fixed to a latch plate 52. In the locking state 150, the bar 36 is aligned such that it doesn't come into contact with the indicator leg 206 of the indicator mechanism 200. The latch unit 61 includes a selection plate 72, an adjustment switch 56, an unlocked state detent 74, a locking state detent 76, and a bias member (not shown). The adjustment switch 56 is fixed to the selection plate 72. The unlocked state detent 74 and the locking state detent 76 are formed in the selection plate 72. The unlocked state detent 74 and the locking state detent 76 are configured to accept a detent pin 78, which is affixed to the handle 26 and assist in restraining movement of the selection plate 72. The locking state 150 is enabled by moving the locking state detent 78 to accept the detent pin 78. The selection plate 72 is selectively movable with the adjustment switch 56 so that either the unlocked state detent 74 or the locking state detent 76 accept the detent pin 78. As will be seen below, the selection plate 72 is in mechanical communication with the latch plate 52. Thus, a movement of the adjustment switch 56 along a switch path 58 is mirrored by the hook latch 60. The handle 26 further includes a rear stop 27 and a forward stop 28 that prevent movement of the selection plate 72 beyond the locking state detent 76 in the event that the locking state detent 76 fails to restrain the selection plate 72.

Figure 2B:
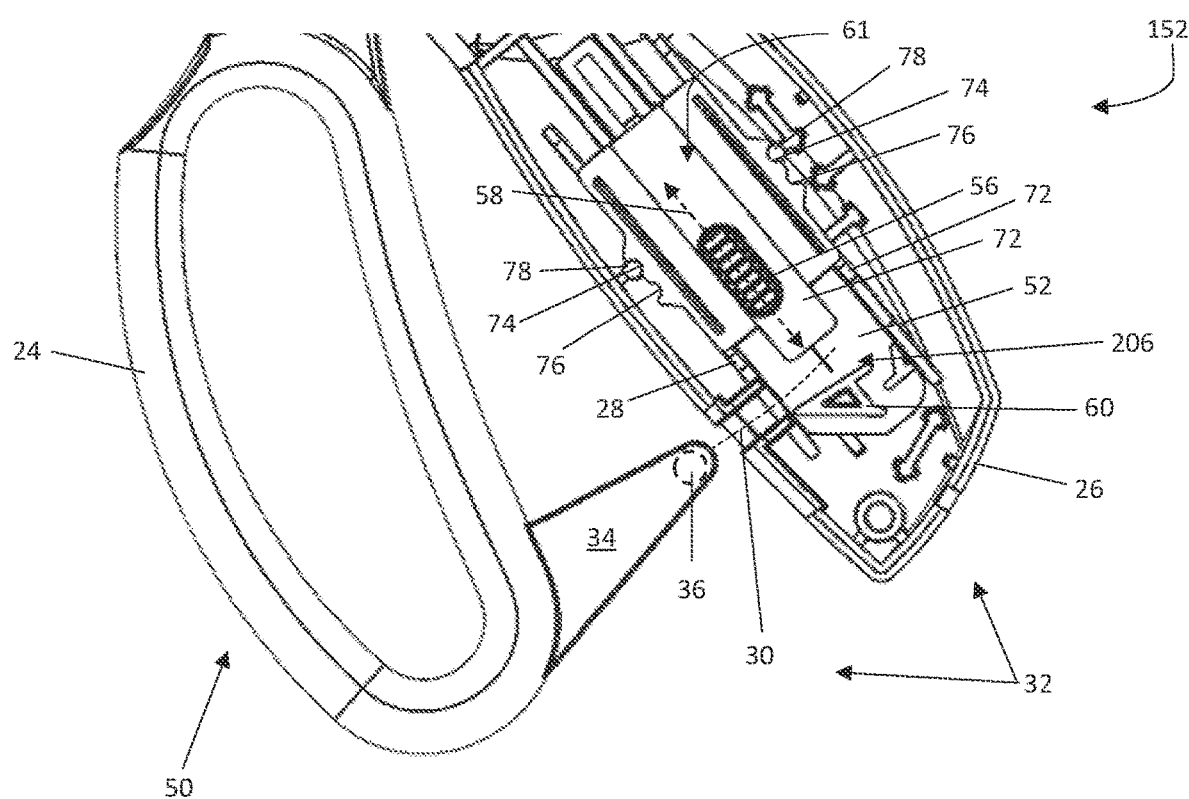
FIG. 2B illustrates a laterally bisected view of a closure assembly.

In FIG. 2B, a closure assembly 32 includes a movement unit 50 and a latch unit 61. The movement unit 50 includes a trigger 24 with a bar arm 34 and a bar 36 extending from the trigger 24, and the latch unit 61 having a selection plate 72 in an unlocked state 152. An indicator leg 206 protrudes from the selection plate 72. The bar 36 is configured to pass through the latching pathway 30 in the handle 26. In the unlocked state 152, the bar 36 is configured to pass by the hook latch 60, which is fixed to the latch plate 52, and be free of contact with the hook latch 60. The latch unit 61 includes the selection plate 72, the adjustment switch 56, the unlocked state detent 74, the locking state detent 76, and the bias member (not shown). The adjustment switch 56 is fixed to the selection plate 72, the unlocked state detent 74, and the locking state detent 76 are formed in the selection plate 72. The unlocked state detent 74 and the locking state detent 76 are configured to accept the detent pin 78, which is affixed to the handle 26. The handle 26 further includes forward stops 28 that restrict movement of the selection plate 72 in the event that the unlocked state detents 74 fail to hold the selection plate 72 in place. The unlocked state 152 is enabled by moving the unlocked state detent 74 to accept the detent pin 78. The selection plate 72 is selectively movable with the adjustment switch 56 so that either the unlocked state detent 74 or the locking state detent 76 accept the detent pin 78. In the unlocked state 152, the bar 36 is aligned such that it comes into contact with the indicator leg 206. As will be seen below, the selection plate 72 is in mechanical communication with the latch plate 52. Thus, a movement of the adjustment switch 56 along the switch path 58 is mirrored by the hook latch 60.

Figure 3A:
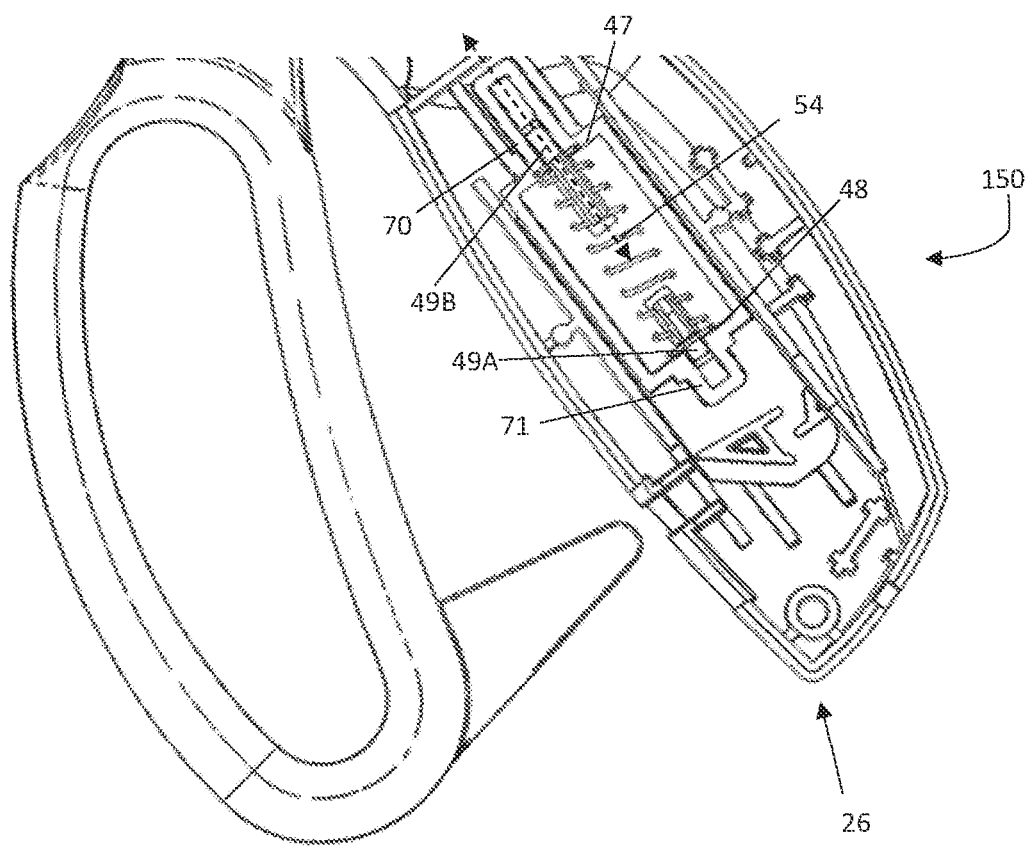
FIG. 3A illustrates a perspective view of the latch unit with an indicator mechanism.

In FIG. 3A, a cross-section of the latch unit 61, in a lockable state 150 is shown in the handle 26. The latch unit 61 includes a rear guide 70, a forward guide 71, a forward movable bias constraint 49A, a rearward movable bias constraint 49B, a forward contact surface 48, a rear contact surface 47, and a bias member 54. The forward movable bias constraint 49A moves within the forward guide 71 to compress the bias member 54. The rearward movable bias constraint 49B moves within the rear guide 70 to compress the bias member 54 in an opposite direction as the forward movable bias constraint 49B.

Figure 3B:
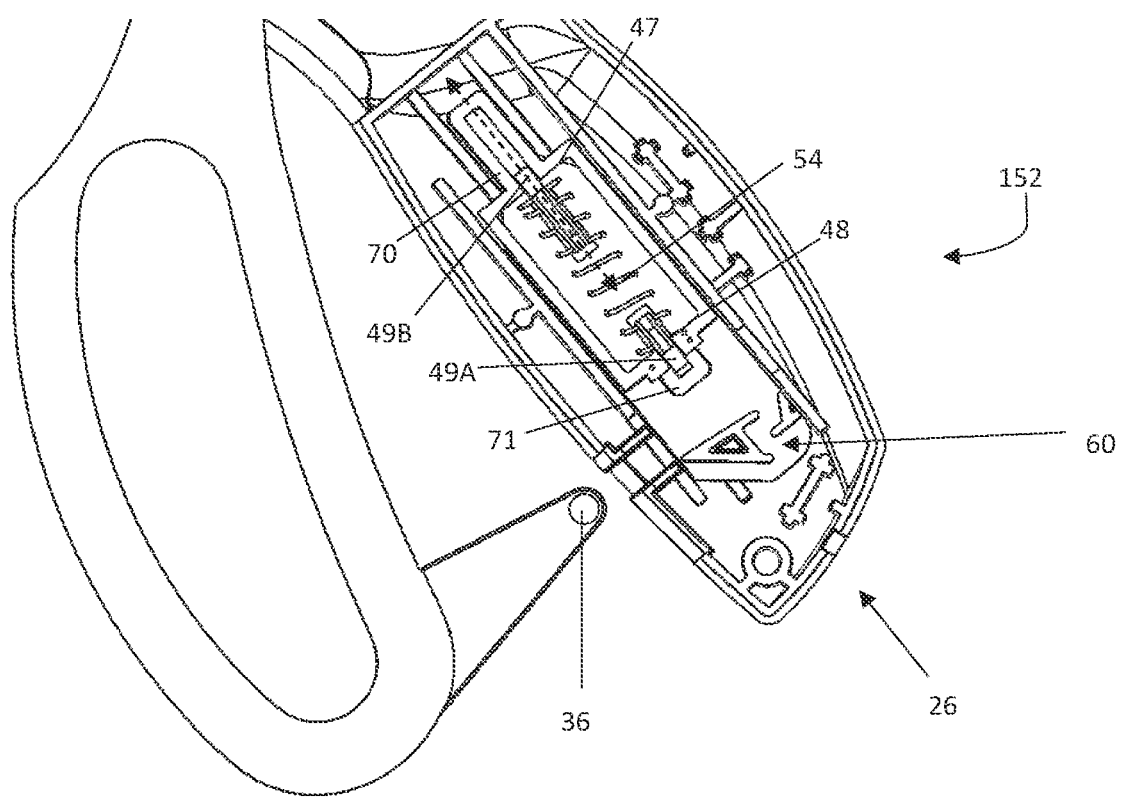
FIG. 3B illustrates a perspective view of the latch unit with an indicator mechanism.

In FIG. 3B, a cross-section of the latch unit 61, in an unlockable state 152 is shown in the handle 26. The latch unit 61 includes a rear guide 70, a forward guide 71, a forward movable bias constraint 49A, a rearward movable bias constraint 49B, a forward contact surface 48, a rear contact surface 47, and a bias member 54. The forward movable bias constraint 49A moves within the forward guide 71. The rearward movable bias constraint 49B moves within the rear guide 70. In an unlockable state 152 the hook latch 60 is moved out of alignment with the bar so that as the bar moved along the prescribed path the bar 36 and hook latch 60 will not contact.

Figure 4:
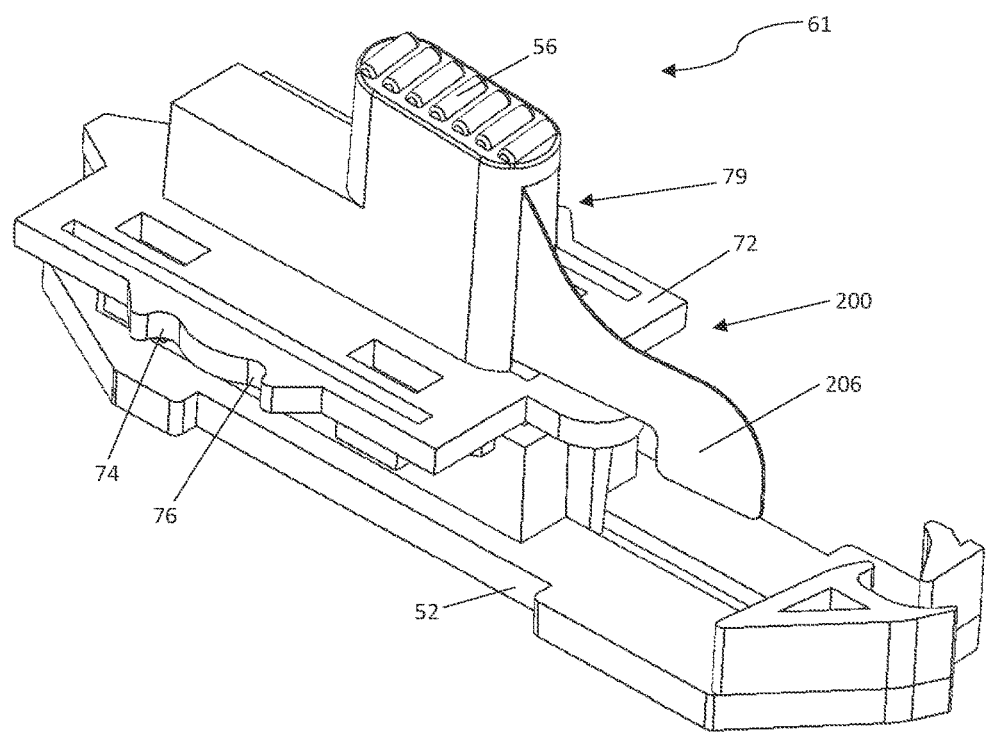
FIG. 4 illustrates a top perspective view of the latch unit and indicator mechanism.

In FIG. 4, the latch unit 61 is shown attached to the latch plate 52. The latch unit 61 includes the selection plate 72, the adjustment switch 56, the unlocked state detent 74, the locking state detent 76, an indicator aperture 79 and the bias member (not shown). An indicator mechanism 200 is housed within the latch unit 61 and includes an indicator leg 206. The indicator leg 206 protrudes from the indicator aperture 79 of the latch unit 61. The selection plate 72 is fixed atop the latch plate 52.

Figure 5A:
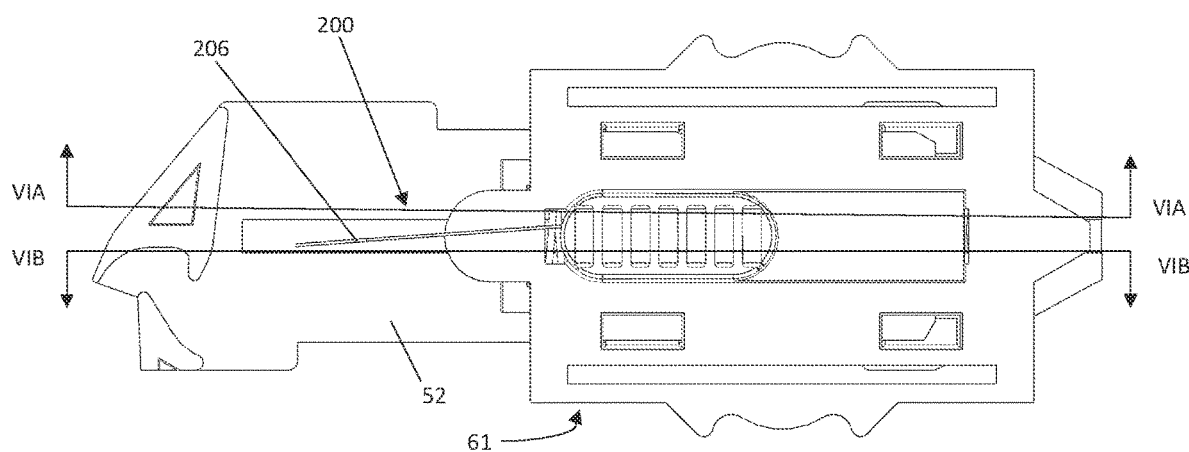
FIG. 5A illustrates a top-down view of the latch unit and indicator mechanism.

FIG. 5A shows latch unit 61 and the latch plate 52. The indicator leg 206 of the indicator mechanism 200 protrudes from the latch unit 61.

Figure 5B:
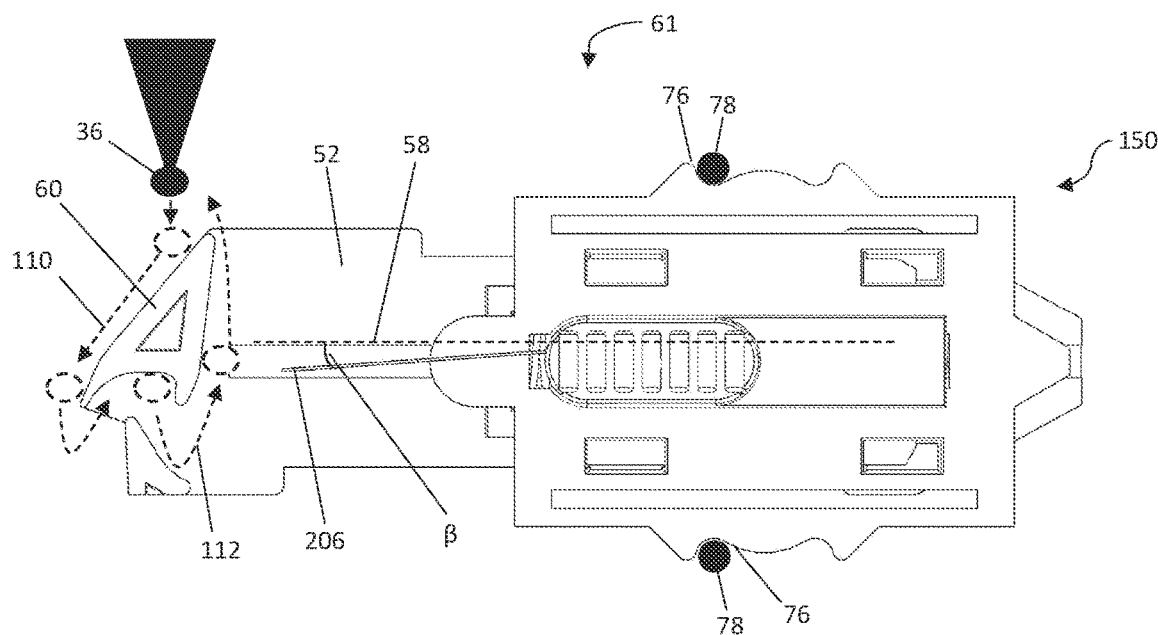
FIG. 5B illustrates a top-down view of the latch unit and latch plate in a lockable state.

FIG. 5B shows the latch unit 61 and latch plate 52 in a lockable state 150. The lockable state 150 is activated when the detent pin 78 is located in the lockable state detent 76. In the lockable state 150, the bar 36 performs a locking movement 110 and an unlocking movement 112 around and remaining in substantially constant contact with the hook latch 60. In the lockable state 150, the bar 36 is prevented from contacting the indicator leg 206. The indicator leg 206 is oriented away from the switch path 58 by an angle β.

Figure 5C:
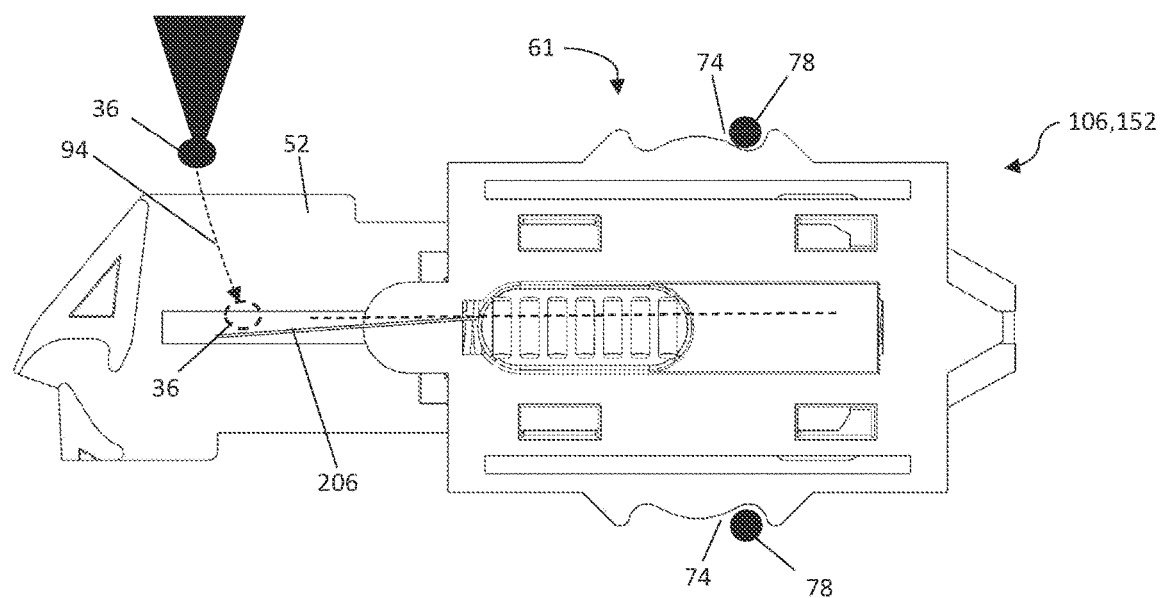
FIG. 5C illustrates a top-down view of the latch unit and latch plate in an unlockable state.

Figure 5C shows the latch unit 61 and latch plate 52 in an unlockable state 152. The unlockable state 152 is activated when the detent pin 78 is located in the unlockable state detent 74. In the unlockable state 152, the bar 36 performs an arcuate movement 94. In the unlockable state 152, the latch plate 52 is in an indicator position 106. The path of the arcuate movement 94 intersects with the indicator leg 206 and fails to intersect with the hook latch 60. The point at which the bar 36 contacts the indicator leg 206 aligns with the pocket 80.

Figure 6A:
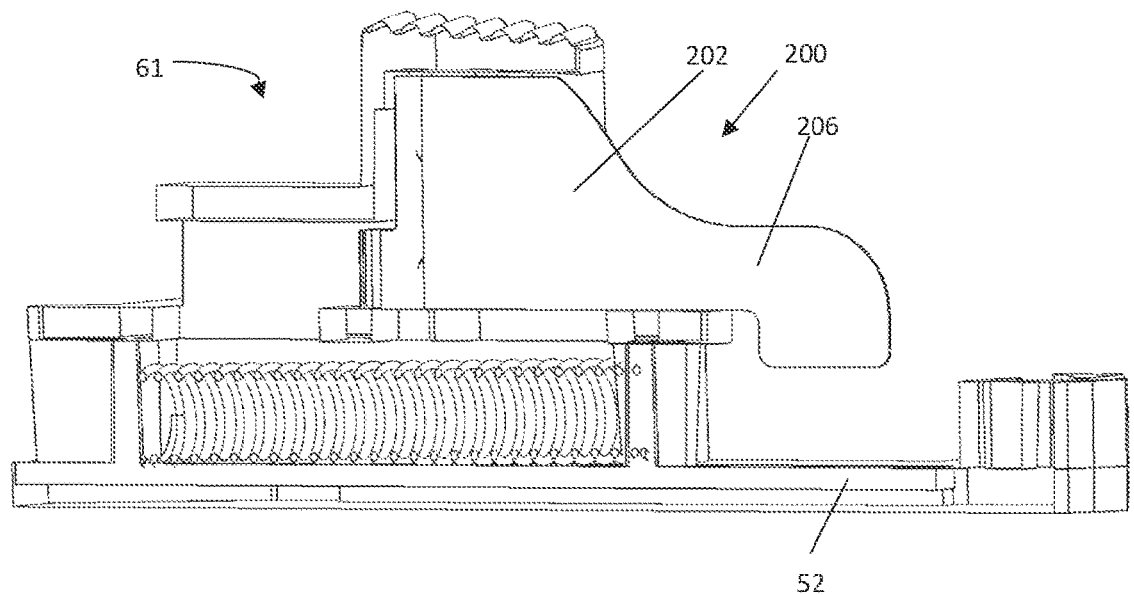
FIG. 6A illustrates the latch unit of FIG. 5A laterally bisected along the line VIA-VIA.

FIG. 6A illustrates the latch unit 61 and latch plate 52 laterally bisected along a line VIA-VIA. The latch unit 61 houses the indicator mechanism 200, including the tab 202 and the indicator leg 206.

Figure 6B:
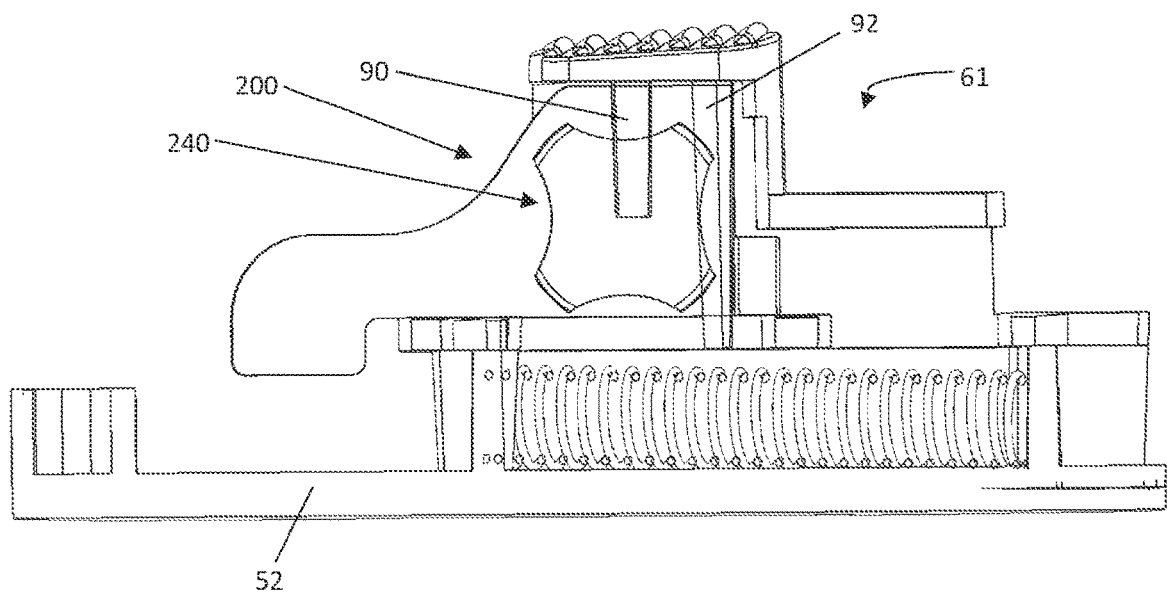
FIG. 6B illustrates the latch unit of FIG. 5A laterally bisected along the line VIB-VIB.

FIG. 6B illustrates the latch unit 61 and latch plate 52 laterally bisected along a line VIB-VIB. The latch unit 61 includes the finger 90 and a connection finger 92. The latch unit 61 houses the indicator mechanism 200 and the dome 240. The dome 240 contacts both the indicator mechanism 200 and the finger 90. The indicator mechanism 200 contacts the connection finger 92.

Figure 7:
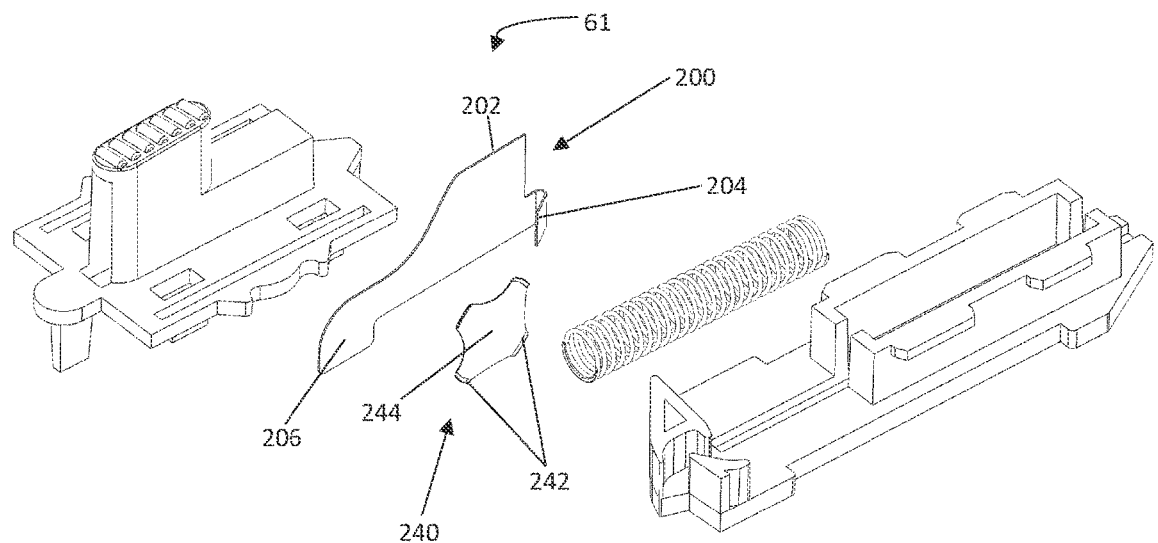
FIG. 7 illustrates an exploded view of the latch unit.

In FIG. 7, the latch unit 61 includes the indicator mechanism 200 and the dome 240. The indicator mechanism 200 includes the indicator leg 206, the tab 202, and the bias tab 204. The dome 240 includes contact legs 242 and a body 244. The dome 240 is oriented on the side of the indicator mechanism 200 where the bias tab 204 extends. The contact legs 242 contact the tab 202 of the indicator mechanism 200.

Figure 8:
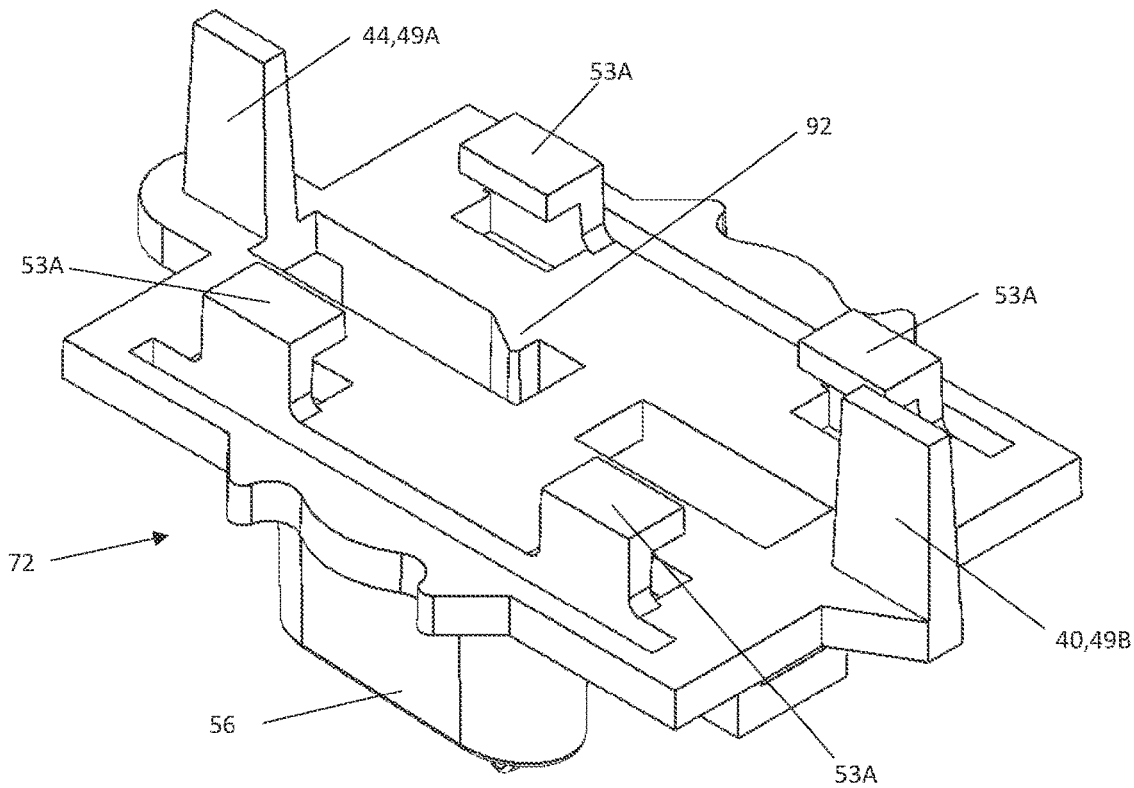
FIG. 8 illustrates an underside view of the selection plate.

In FIG. 8, the selection plate 72 is shown including tracks 53A, a forward post 44, a rear post 40, and a connection finger 92. The forward post 44 is a forward movable bias constraint 49A and the rear post is a rearward movable bias constraint 49B. The connection finger 92 extends toward the adjustment switch 56.

Figure 9:
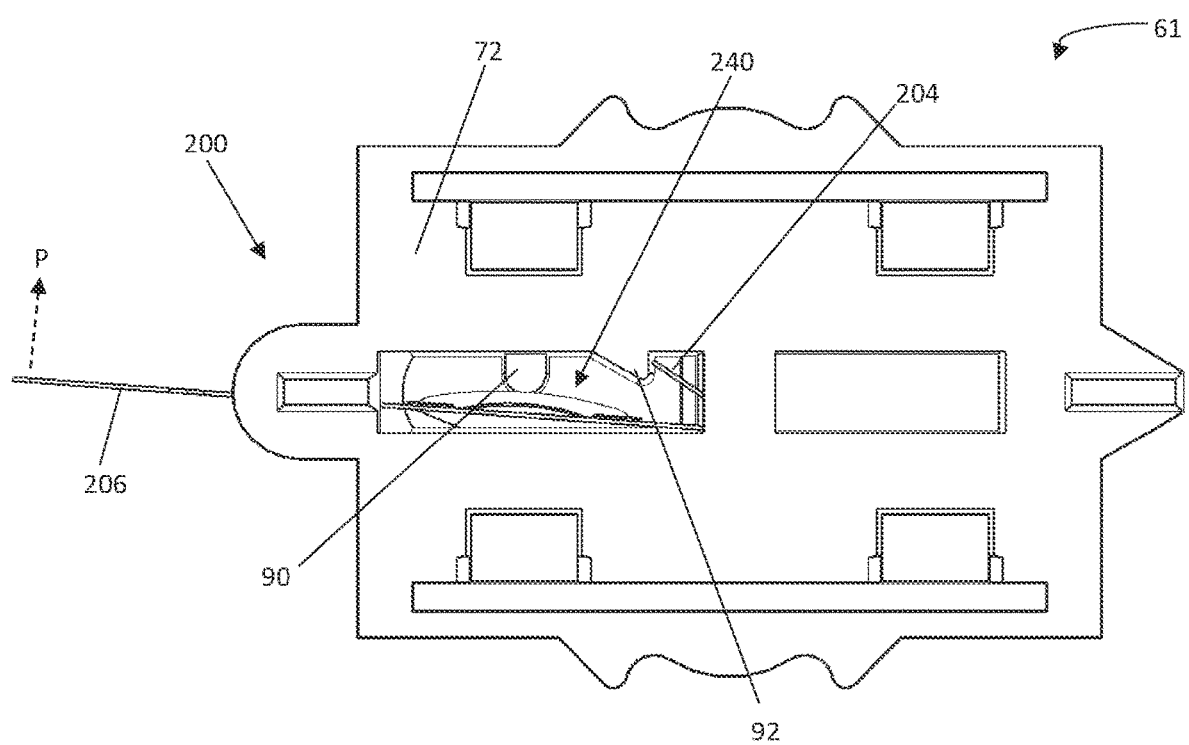
FIG. 9 illustrates an underside view of the latch unit including the indicator mechanism and the dome.

In FIG. 9, the latch unit 61 is shown. The latch unit 61 includes the indicator mechanism 200, the dome 240, and the selection plate 72. The bias tab 204 of the indicator mechanism 200 contacts the connection finger 92, preventing axial detachment of the indicator mechanism 200 and enabling rotational movement of the indicator mechanism 200 within the selection plate 72. The dome 240 contacts the indicator mechanism 200 and the finger 90. As the bar (not shown) contacts the indicator leg 206 of the indicator mechanism 200, the indicator leg 206 is biased along the indicator path P. Bias of the indicator leg 206 depresses the dome 240 against the finger 90. The dome 240 produces audible feedback when the dome 240 is depressed.

Figure 10A:
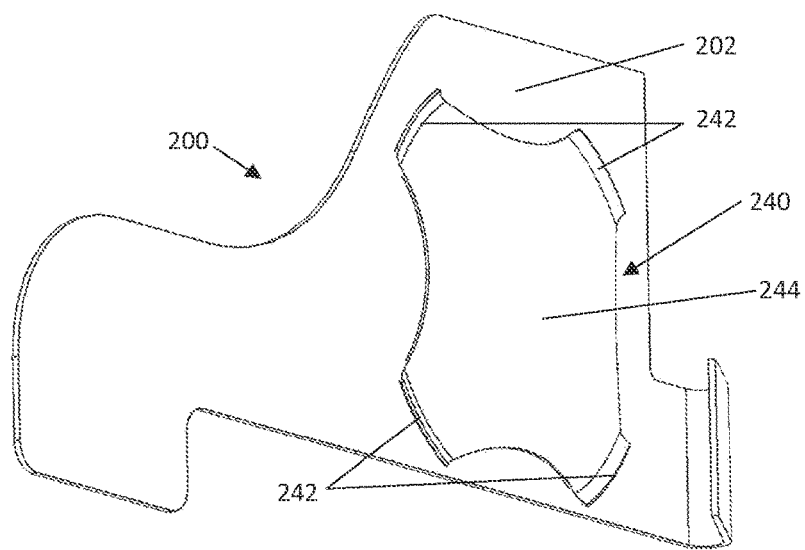
FIG. 10A illustrates a perspective view of the indicator mechanism including a dome.

In FIG. 10A, the indicator mechanism 200 and the dome 240 are shown. The indicator legs 242 of the dome 240 contact the tab 202 and raise the body 244 away from the tab 202.

Figure 10B:
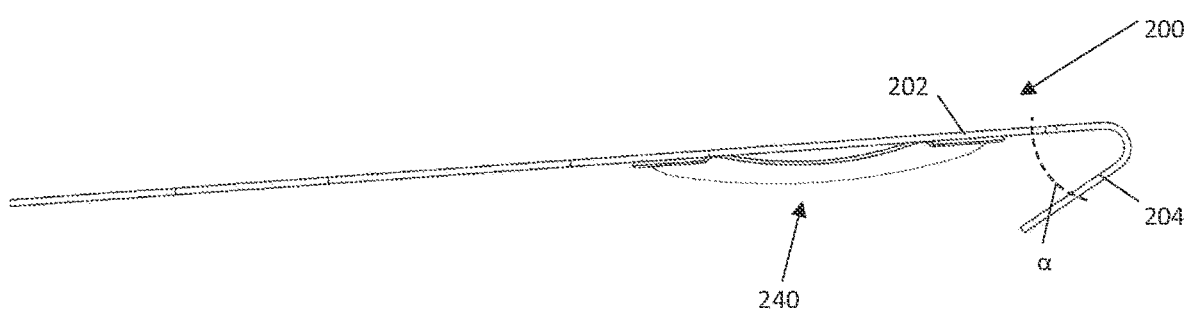
FIG. 10B illustrates a top-down view of the indicator mechanism and the dome.

In FIG. 10B, the indicator mechanism 200 and the dome 240 are shown. The bias tab 204 of the indicator mechanism 200 is oriented an angle α from the tab 202.

Figure 11:
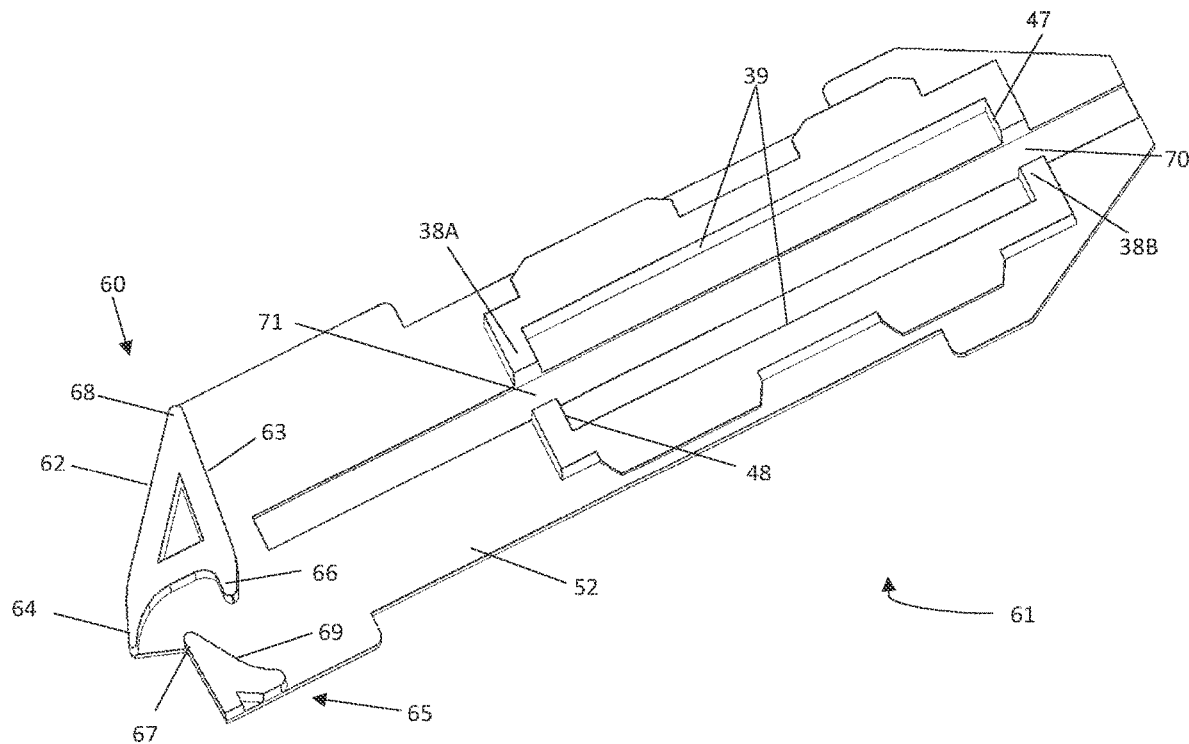
FIG. 11 illustrates a perspective view of the latch plate.

FIG. 11 illustrates a perspective view of the latch plate 52. The latch plate 52 includes a rearward bias constraint 38B, a forward bias constraint 38A, a rear contact surface 47, a forward contact surface 48, side bias constraints 39, a forward guide 71, a rear guide 70, a hook latch 60, and a wall guide 65. The hook latch 60 includes an entry portion 62, an entry apex 64, an exit apex 66, a return portion 63, and a release apex 68. The wall guide 65 includes a guide apex 67 and a rear wall 69.

Figure 12:
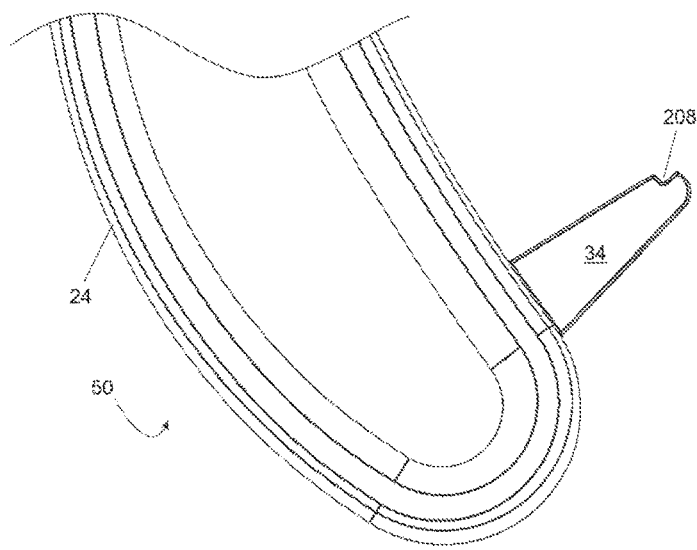
FIG. 12 illustrates a close-up view of a bar arm including a contact element shown as a notch.

FIG. 12 is a close-up view of a movement unit 50. The movement unit 50 is a trigger 24 including a bar arm 34 with a notch 208. When the trigger 24 is moved towards the handle (not shown) the notch 208 contacts the indicator leg of the indicator mechanism (not shown) creating an indication.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A closure assembly for a surgical device comprising:
 a movement unit including a contact element that is movable in a direction of a prescribed motion between a first position and a second position;
 a latch unit including a latch plate and a latch member extending from the latch plate, the latch plate being movable between:
   a lockable state where the latch member is engageable by the contact element; and
   an unlockable state where the latch member is not engageable by the contact element; and
 an indicator mechanism configured to generate an indication when the latch unit is in the unlockable state and the contact element is moved to the second position.

2. The closure assembly of claim 1, wherein the indication is a tactile indication.

3. The closure assembly of claim 1, wherein the indication is an audible indication.

4. The closure assembly of claim 1, wherein the indication is a visual indication.

5. The closure assembly of claim 1, wherein the indication is electronic and results in a light being turned on, a light being turned off, an audible signal being created, tactile feedback being generated, or a combination thereof.

6. The closure assembly of claim 1, wherein the contact element is a bar.

7. The closure assembly of claim 1, wherein the contact element is a notch formed in a bar arm of the movement unit.

8. The closure assembly of claim 1, wherein the movement unit includes a trigger operably coupled to the contact element, and wherein actuation of the trigger causes the contact element to move in the direction of the prescribed motion.

9. The closure assembly of claim 1, wherein the indicator mechanism is connected to the latch plate and the indicator mechanism is unreachable by the contact element when the latch plate is in the lockable state.

10. A closure assembly for a surgical device comprising:
 a movement unit including a bar, the bar movable in a direction of a prescribed motion between a first position and a second position;
 a latch unit including a latch member, the latch member being movable between:
   a lockable state where the latch member is engageable by the bar; and
   an unlockable state where the latch member is not engageable by the bar; and
 an indicator mechanism configured to generate an indication when the latch unit is in the unlockable state and the bar is moved to the second position.

11. The closure assembly of claim 10, wherein the latch member extends from a movable latch plate of the latch unit.

12. The closure assembly of claim 11, wherein the latch member is a hook latch.

13. The closure assembly of claim 11, wherein the latch unit further includes a selection plate that is in mechanical communication with the latch plate.

14. The closure assembly of claim 13, wherein the latch unit further includes an adjustment switch that is coupled to the selection plate, and wherein movement of the adjustment switch along a switch path causes movement of the latch member between the lockable and unlockable states.

15. The closure assembly of claim 10, wherein the indication is at least one of a tactile indication, an audible indication, or a visual indication.

16. The closure assembly of claim 10, wherein the indication is electronic and results in a light being turned on, a light being turned off, an audible signal being created, tactile feedback being generated, or a combination thereof.

17. A closure assembly for a surgical device comprising:
 a movement unit including a contact element that is movable in a direction of a prescribed motion between a first position and a second position;
 a latch unit including a latch member that is movable between an activated state where the latch member is engageable by the contact element when the contact element moves from the first position to the second position and a deactivated state where the latch member is not engageable by the contact element when the contact element is moved from the first position to the second position; and
 an indicator mechanism configured to generate at least one of tactile feedback, audible feedback, or visual feedback when the latch unit is in the deactivated state and the contact element is moved to the second position.

18. The closure assembly of claim 17, wherein contact between the indicator mechanism and the contact element generates the at least one of the tactile feedback, the audible feedback, or the visual feedback.

19. The closure assembly of claim 17, wherein movement of the latch member between the activated state and the deactivated state is controlled by a switch that is operably coupled to the latch member.

20. The closure assembly of claim 17, wherein the movement unit further includes a trigger operably coupled to the contact element, and wherein actuation of the trigger causes the contact element to move in the direction of the prescribed motion.

* * * * *